(12) United States Patent  
Carlton et al.

(10) Patent No.: US 9,207,845 B2  
(45) Date of Patent: Dec. 8, 2015

(54) SYSTEM AND METHOD FOR ATLAS REGISTRATION

(75) Inventors: Keith Carlton, Boston, MA (US); David Arthur Blum, Boston, MA (US); Michael A. Moffitt, Valencia, CA (US); Scott Kokones, Boston, MA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 591 days.

(21) Appl. No.: 13/431,232

(22) Filed: Mar. 27, 2012

(65) Prior Publication Data

US 2012/0314924 A1 Dec. 13, 2012

Related U.S. Application Data

(60) Provisional application No. 61/468,884, filed on Mar. 29, 2011, provisional application No. 61/468,887, filed on Mar. 29, 2011, provisional application No. 61/468,891, filed on Mar. 29, 2011, provisional application No. 61/468,897, filed on Mar. 29, 2011, provisional application No. 61/468,901, filed on Mar. 29, 2011.

(51) Int. Cl.  
*G06K 9/00* (2006.01)  
*G06F 3/0484* (2013.01)  
(Continued)

(52) U.S. Cl.  
CPC ............ *G06F 3/04845* (2013.01); *A61B 19/56* (2013.01); *G06F 3/04815* (2013.01); *G06F 19/321* (2013.01); *G06T 3/4038* (2013.01); *G06T 7/0012* (2013.01); *G06T 7/0024* (2013.01); *G06T 11/60* (2013.01); *G06T 19/00* (2013.01); *G06F 19/3481* (2013.01);

(Continued)

(58) Field of Classification Search  
CPC .................................................. G06K 9/6206  
See application file for complete search history.

(56) References Cited

U.S. PATENT DOCUMENTS 5,099,846 A 3/1992 Hardy  
5,361,763 A 11/1994 Kao et al.  
(Continued)

FOREIGN PATENT DOCUMENTS

WO 01/90876 A1 11/2001  
WO 2007/097859 A1 8/2007  
(Continued)

OTHER PUBLICATIONS

Castro et al., "A cross validation study of deep brain stimulation targeting: from experts to atlas-based, segmentation-based and automatic registration algorithms", IEEE Transactions on Medical Imaging, vol. 25, No. 11, Nov. 2006.*

(Continued)

*Primary Examiner* — Soo Park  
(74) *Attorney, Agent, or Firm* — Lowe Graham Jones PLLC; Bruce E. Black

(57) ABSTRACT

A system and method for associating anatomically significant regions with regions of one or more images may include automatically modifying images of different modalities according to different correction algorithms, providing a user interface for identifying a plane within three-dimensional data, scaling atlas structures to fit an anatomical image according to identified landmarks, registering an atlas to such an image via a combination of registration algorithms, and/or registering an atlas to such an image using a feature extraction algorithm.

27 Claims, 18 Drawing Sheets

(51) Int. Cl.
*G06F 19/00* (2011.01)
*G06T 19/00* (2011.01)
*G06T 7/00* (2006.01)
*G06T 3/40* (2006.01)
*A61B 19/00* (2006.01)
*G06F 3/0481* (2013.01)
*G06T 11/60* (2006.01)

(52) U.S. Cl.
CPC .......... G06T2207/10072 (2013.01); *G06T 2207/30016* (2013.01); *G06T 2219/028* (2013.01)

(56) References Cited

U.S. PATENT DOCUMENTS

| | | |
|---|---|---|
| 5,452,407 A | 9/1995 | Crook |
| 5,782,762 A | 7/1998 | Vining |
| 5,938,688 A | 8/1999 | Schiff |
| 6,066,163 A | 5/2000 | John |
| 6,083,162 A | 7/2000 | Vining |
| 6,106,460 A | 8/2000 | Panescu et al. |
| 6,240,308 B1 | 5/2001 | Hardy et al. |
| 6,289,239 B1 | 9/2001 | Panescu et al. |
| 6,310,619 B1 | 10/2001 | Rice |
| 6,319,241 B1 | 11/2001 | King et al. |
| 6,351,675 B1 | 2/2002 | Tholen et al. |
| 6,389,311 B1 | 5/2002 | Whayne et al. |
| 6,463,328 B1 | 10/2002 | John |
| 6,491,699 B1 | 12/2002 | Henderson et al. |
| 6,539,263 B1 | 3/2003 | Schiff et al. |
| 6,622,048 B1 | 9/2003 | Mann et al. |
| 6,690,972 B2 | 2/2004 | Conley et al. |
| 6,694,162 B2 | 2/2004 | Hartlep |
| 6,694,163 B1 | 2/2004 | Vining |
| 6,748,098 B1 | 6/2004 | Rosenfeld |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,909,913 B2 | 6/2005 | Vining |
| 7,003,349 B1 | 2/2006 | Andersson et al. |
| 7,003,352 B1 | 2/2006 | Whitehurst |
| 7,008,370 B2 | 3/2006 | Tanner et al. |
| 7,035,690 B2 | 4/2006 | Goetz |
| 7,043,293 B1 | 5/2006 | Baura |
| 7,050,857 B2 | 5/2006 | Samuelsson et al. |
| 7,107,102 B2 | 9/2006 | Daignault, Jr. et al. |
| 7,136,518 B2 | 11/2006 | Griffin et al. |
| 7,136,695 B2 | 11/2006 | Pless et al. |
| 7,146,219 B2 | 12/2006 | Sieracki et al. |
| 7,146,223 B1 | 12/2006 | King |
| 7,151,961 B1 | 12/2006 | Whitehurst et al. |
| 7,155,279 B2 | 12/2006 | Whitehurst et al. |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,209,787 B2 | 4/2007 | DiLorenzo |
| 7,216,000 B2 | 5/2007 | Sieracki et al. |
| 7,217,276 B2 | 5/2007 | Henderson et al. |
| 7,218,968 B2 | 5/2007 | Condie et al. |
| 7,231,254 B2 | 6/2007 | DiLorenzo |
| 7,239,910 B2 | 7/2007 | Tanner |
| 7,239,926 B2 | 7/2007 | Goetz |
| 7,242,984 B2 | 7/2007 | DiLorenzo |
| 7,252,090 B2 | 8/2007 | Goetz |
| 7,254,446 B1 | 8/2007 | Erickson et al. |
| 7,257,447 B2 | 8/2007 | Cates et al. |
| 7,266,412 B2 | 9/2007 | Stypulkowski |
| 7,295,876 B1 | 11/2007 | Erickson |
| 7,313,430 B2 | 12/2007 | Urquhart et al. |
| 7,324,851 B1 | 1/2008 | DiLorenzo |
| 7,346,382 B2 | 3/2008 | McIntyre et al. |
| 7,388,974 B2 | 6/2008 | Yanagita |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,603,177 B2 | 10/2009 | Sieracki et al. |
| 7,617,002 B2 | 11/2009 | Goetz |
| 7,623,918 B2 | 11/2009 | Goetz |
| 7,657,319 B2 | 2/2010 | Goetz et al. |
| 7,676,273 B2 | 3/2010 | Goetz et al. |
| 7,848,802 B2 | 12/2010 | Goetz et al. |
| 2004/0044279 A1 | 3/2004 | Lewin et al. |
| 2004/0106916 A1 | 6/2004 | Quaid et al. |
| 2004/0199216 A1 | 10/2004 | Lee et al. |
| 2004/0267330 A1 | 12/2004 | Lee et al. |
| 2005/0070781 A1 | 3/2005 | Dawant et al. |
| 2005/0171587 A1 | 8/2005 | Daglow et al. |
| 2006/0017749 A1 | 1/2006 | McIntyre et al. |
| 2006/0020292 A1 | 1/2006 | Goetz et al. |
| 2006/0235472 A1 | 10/2006 | Goetz et al. |
| 2006/0259079 A1 | 11/2006 | King |
| 2007/0017749 A1 | 1/2007 | Dold et al. |
| 2007/0049817 A1 | 3/2007 | Preiss et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0156186 A1 | 7/2007 | Lee et al. |
| 2007/0162086 A1 | 7/2007 | DiLorenzo |
| 2007/0185544 A1 | 8/2007 | Dawant et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0071150 A1 | 3/2008 | Miesel et al. |
| 2008/0081982 A1 | 4/2008 | Simon et al. |
| 2008/0103533 A1 | 5/2008 | Patel et al. |
| 2008/0123922 A1 | 5/2008 | Gielen et al. |
| 2008/0141217 A1 | 6/2008 | Goetz et al. |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0215118 A1 | 9/2008 | Goetz et al. |
| 2008/0269588 A1 | 10/2008 | Csavoy et al. |
| 2009/0112289 A1 | 4/2009 | Lee et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0204192 A1 | 8/2009 | Carlton et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010646 A1 | 1/2010 | Drew et al. |
| 2010/0049276 A1 | 2/2010 | Blum et al. |
| 2010/0049280 A1 | 2/2010 | Goetz |
| 2012/0027272 A1* | 2/2012 | Akinyemi et al. ............ 382/128 |

(56) References Cited

U.S. PATENT DOCUMENTS

FOREIGN PATENT DOCUMENTS

| WO | 2007/100427 | A1 | 9/2007 |
| WO | 2007/100428 | A1 | 9/2007 |
| WO | 2007/112061 | A2 | 10/2007 |

OTHER PUBLICATIONS

Bazin et al., "Free software tools for atlas-based volumetric neuroimage analysis", Proc. SPIE 5747, Medical Imaging 2005: Image Processing, 1824 May 5, 2005.*
Butson et al., "Current Steering to Control the Volume of Tissue Activated During Deep Brain Stimulation," Brain Stimulation 1, 2008, pp. 7-15.
Butson et al., "Patient-Specific Analysis of the Volume of Tissue Activated During Deep Brain Stimulation," Neuroimage 34, 2007, pp. 661-670.
Butson et al., "Role of Electrode Design on the Volume of Tissue Activated During Deep Brain Stimulation," Journal of Neural Engineering, Mar. 1, 2006, vol. 3, No. 1, pp. 1-8.
Butson et al., "StimExplorer: Deep Brain Stimulation Parameter Selection Software System," Acta Neurochirugica, Jan. 1, 2007, vol. 97, No. 2, pp. 569-574.
Miocinovic et al., "Cicerone: Stereotactic Neurophysiological Recording and Deep Brain Stimulation Electrode Placement Software System," Acta Neurochirurigica Suppl., Jan. 1, 2007, vol. 97, No. 2, pp. 561-567.
Schmidt et al., "Sketching and Composing Widgets for 3D Manipulation," Eurographics, Apr. 2008, vol. 27, No. 2, pp. 301-310.
PCT Search Report from PCT/US09/03017, dated Aug. 3, 2009.
PCT Search Report from PCT/US09/03038, dated Oct. 8, 2009.
PCT Search Report from PCT/US09/03040, dates Aug. 13, 2009.
PCT Search Report from PCT/US09/03041, dated Aug. 20, 2009.
PCT Search Report from PCT/US09/03049, dated Jan. 26, 2010.

* cited by examiner

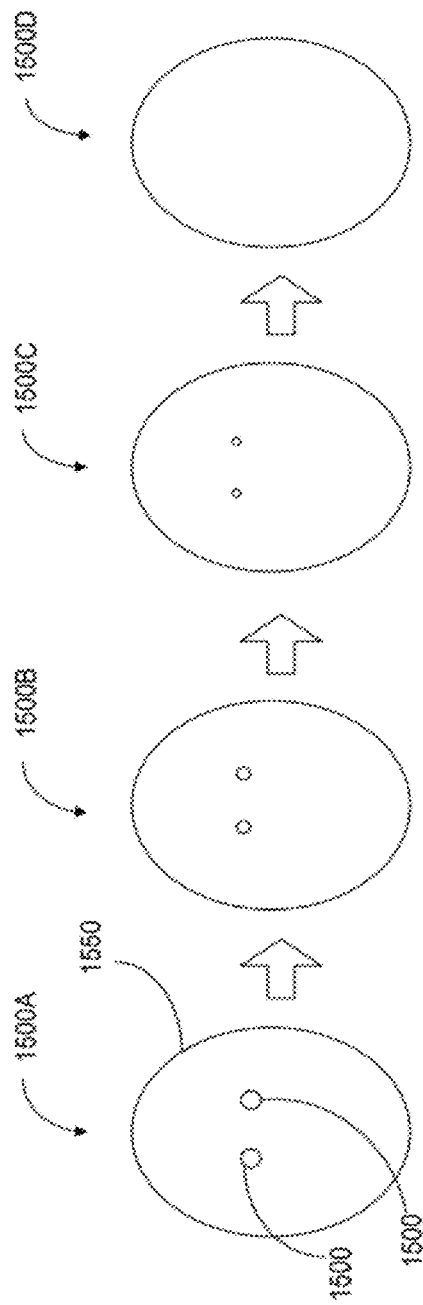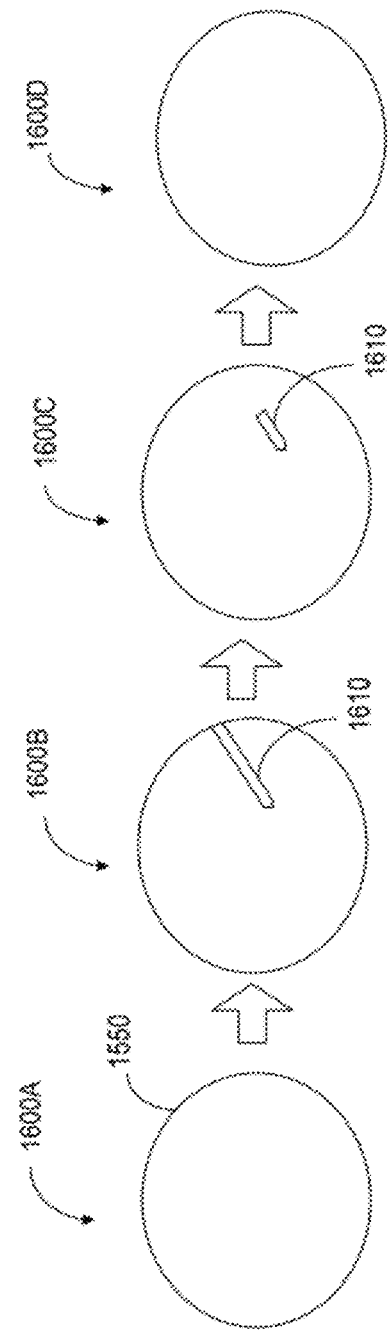

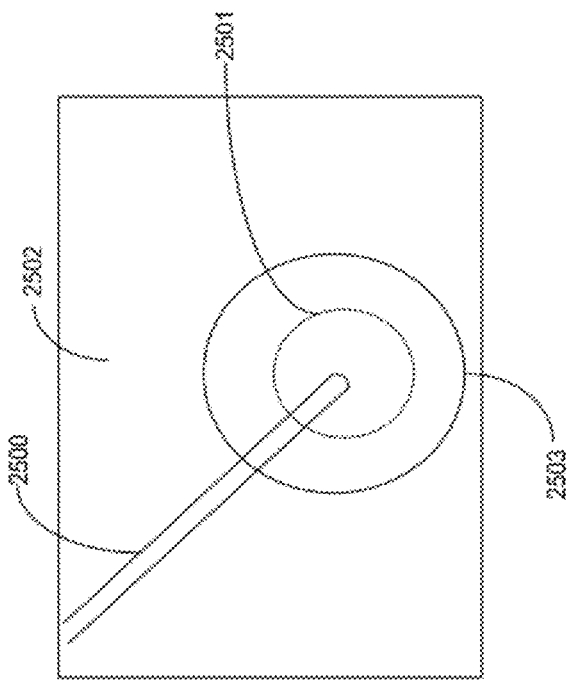
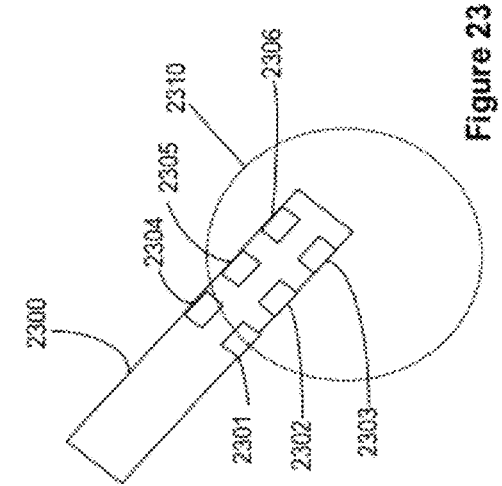
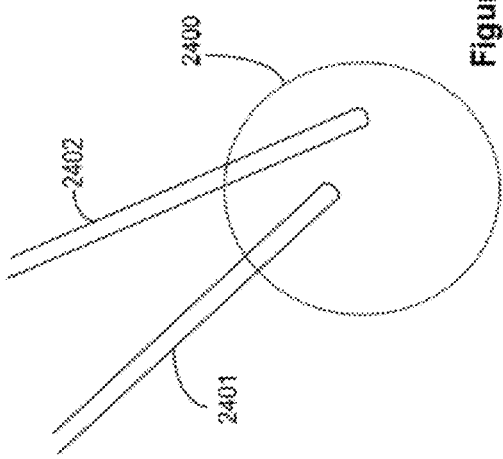

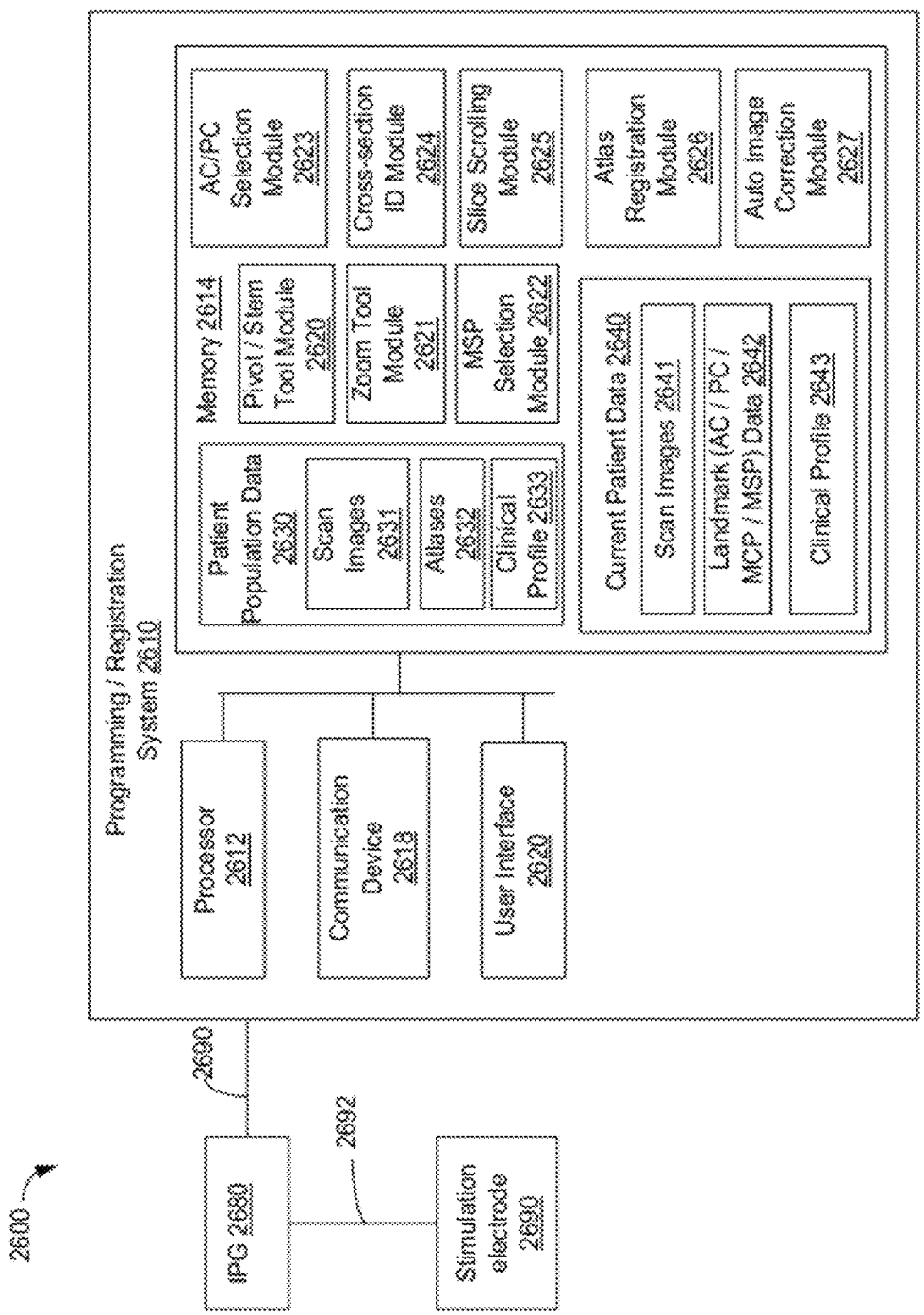

SYSTEM AND METHOD FOR ATLAS REGISTRATION

CROSS-REFERENCE TO RELATED APPLICATIONS

This application claims the benefit, under 35 U.S.C. §119 (e), of U.S. Provisional Patent Application Ser. Nos. 61/468,884, 61/468,887, 61/468,891, 61/468,897 and 61/468,901, filed Mar. 29, 2011, the entire contents of which are hereby incorporated by reference.

FIELD OF THE INVENTION

The present invention relates to a system and method for surgical planning for implanting a stimulation leadwire, registration of images for generating a model via which to determine how to apply a stimulation, for programming stimulation settings, and/or for applying a therapeutic stimulation, and/or for integration of components providing such functionality.

BACKGROUND

Electrical stimulation of an anatomical region, e.g., deep brain stimulation (DBS), such as of the thalamus or basal ganglia, is a clinical technique for the treatment of disorders such as essential tremor, Parkinson's disease (PD), and other physiological disorders. DBS may also be useful for traumatic brain injury and stroke. Pilot studies have also begun to examine the utility of DBS for treating dystonia, epilepsy, and obsessive-compulsive disorder.

A stimulation procedure, such as DBS, typically involves first obtaining preoperative images, e.g., of the patient's brain, such as by using a computed tomography (CT) scanner device, a magnetic resonance imaging (MRI) device, or any other imaging modality. This sometimes involves first affixing to the patient's skull spherical or other fiducial markers that are visible on the images produced by the imaging modality. The fiducial markers help register the preoperative images to the actual physical position of the patient in the operating room during the later surgical procedure.

After the preoperative images are acquired by the imaging modality, they are then loaded onto an image-guided surgical (IGS) workstation, and, using the preoperative images displayed on the IGS workstation, a neurosurgeon can select a target region, e.g., within the brain, an entry point, e.g., on the patient's skull, and a desired trajectory between the entry point and the target region. The entry point and trajectory are typically carefully selected to avoid intersecting or otherwise damaging certain nearby critical structures or vasculature, e.g., of the brain.

In the operating room, the physician marks the entry point on the patient's skull, drills a burr hole at that location, and affixes a trajectory guide device about the burr hole. The trajectory guide device includes a bore that can be aimed to obtain the desired trajectory to the target region. After aiming, the trajectory guide is locked to preserve the aimed trajectory toward the target region. After the aimed trajectory has been locked in using the trajectory guide, a microdrive introducer is used to insert the surgical instrument along the trajectory toward the target region, e.g., of the brain. The surgical instrument may include, among other things, a recording electrode leadwire, for recording intrinsic electrical signals, e.g., of the brain; a stimulation electrode leadwire, for providing electrical energy to the target region, e.g., of the brain; or associated auxiliary guidewires or guide catheters for steering a primary instrument toward the target region, e.g., of the brain.

The stimulation electrode leadwire, which typically includes multiple closely-spaced electrically independent stimulation electrode contacts, is then introduced to deliver the therapeutic stimulation to the target region, e.g., of the brain. The stimulation electrode leadwire is then immobilized, such as by using an instrument immobilization device located at the burr hole entry, e.g., in the patient's skull, in order for the DBS therapy to be subsequently performed.

The subthalamic nucleus (STN) represents the most common target for DBS technology. Clinically effective STN DBS for PD has typically used electrode contacts in the anterior-dorsal STN. However, STN DBS exhibits a low threshold for certain undesirable side effects, such as tetanic muscle contraction, speech disturbance and ocular deviation. Highly anisotropic fiber tracks are located about the STN. Such nerve tracks exhibit high electrical conductivity in a particular direction. Activation of these tracks has been implicated in many of the DBS side effects. However, there exists a limited understanding of the neural response to DBS. The three-dimensional (3-D) tissue medium near the DBS electrode typically includes both inhomogeneous and anisotropic characteristics. Such complexity makes it difficult to predict the particular volume of tissue influenced by DBS.

After the immobilization of the stimulation electrode leadwire, the actual stimulation therapy is often not initiated until after a time period of about two-weeks to one month has elapsed. This is due primarily to the acute reaction of the brain tissue to the introduced electrode leadwire (e.g., the formation of adjacent scar tissue), and stabilization of the patient's disease symptoms. At that time, a particular one or more of the stimulation electrode contacts is selected for delivering the therapeutic stimulation, and other stimulation parameters are adjusted to achieve an acceptable level of therapeutic benefit.

A system and method may estimate stimulation volumes, and display models of a patient anatomy and/or a stimulation leadwire, via which to graphically identify the estimated stimulation volumes and how they interact with various regions of the patient anatomy, for example, as described in U.S. patent application Ser. No. 12/454,330, filed May 15, 2009 ("the '330 application"), U.S. patent application Ser. No. 12/454,312, filed May 15, 2009 ("the '312 application"), U.S. patent application Ser. No. 12/454,340, filed May 15, 2009 ("the '340 application"), U.S. patent application Ser. No. 12/454,343, filed May 15, 2009 ("the '343 application"), and U.S. patent application Ser. No. 12/454,314, filed May 15, 2009 ("the '314 application"), the content of each of which is hereby incorporated herein by reference in its entirety.

SUMMARY

Example embodiments of the present invention provide a system that includes modules providing respective user interfaces via which to perform surgical planning, image and atlas registration, and stimulation programming. The user interfaces may be graphical user interfaces (GUI) displayed in a display device. The display device may be any suitably appropriate display device.

Embodiments of the present invention facilitate image registration used for accurate modeling of the patient anatomy, stimulation leadwire, estimated stimulation volumes, and interactions of stimulation volumes with the patient anatomy.

Various systems, system components, and/or program modules may be used for performance of various tasks associated with, or that provide an output usable for, providing therapeutic stimulation. Embodiments of the present invention provide for communication and/or between the various systems, system components, and/or program modules.

Example embodiments of the present invention provide methods by which to select target areas to stimulate, target stimulation parameters, and/or target stimulation hardware.

An example embodiment of the present invention provides a method by which to output estimated volumes of activation (VOAs) in a short processing time.

The various methods described herein may be practiced, each alone, or in various combinations.

An example embodiment of the present invention is directed to a processor, which may be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination. The memory device may include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to a hardware computer-readable medium, e.g., as described above, having stored thereon instructions executable by a processor to perform the methods described herein.

An example embodiment of the present invention is directed to a method, e.g., of a hardware component or machine, of transmitting instructions executable by a processor to perform the methods described herein.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

FIG. 15 shows a series of images representing axial CT slices that include features corresponding to cross sections of leadwires, according to an example embodiment of the present invention.

FIG. 16 shows a series of images representing sagittal CT slices that include features corresponding to cross sections of leadwires, according to an example embodiment of the present invention.

FIG. 23 shows a single leadwire positioned relative to a target volume of activation, according to an example embodiment of the present invention.

FIG. 24 shows a pair of leadwires positioned relative to a target volume of activation, according to an example embodiment of the present invention.

FIG. 25 shows an image of a maximum volume of activation displayed according to an example embodiment of the present invention.

FIG. 26 shows a block diagram of a patient registration system, according to an example embodiment of the present invention.

DETAILED DESCRIPTION

Figure 1:
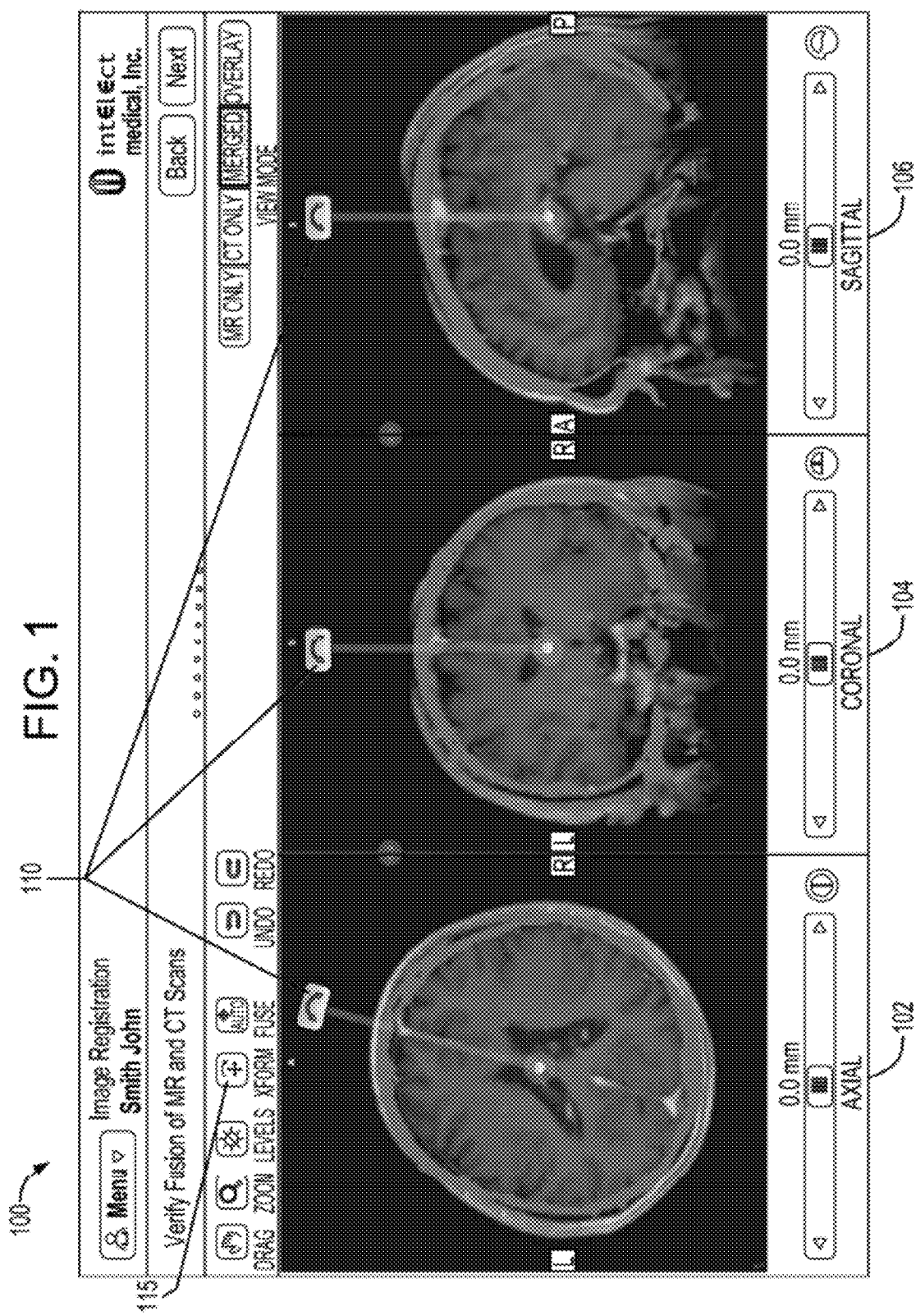
FIG. 1 is a screen shot showing a pivot and stem tool, according to an example embodiment of the present invention.

Fuse Images Using a Pivot and Stem Transformation Tool and See Live Updates from all Three Planes It may be advantageous or necessary to correctly position relative to each other in a system memory various relevant features of a patient anatomy, or features positioned relative to the a patient anatomy. Such relative positioning may be useful, for example, for correctly outputting a graphical depiction of such features, on which basis a clinician may determine how to program stimulation settings, and/or for the system to accurately determine stimulation settings to use, estimated VOAs, and/or target VOAs. Different subsets of such features may be identifiable in different patient images, which may be, for example, of different imaging modalities. For example, certain features may be readily identifiable in a magnetic resonance (MR) image, while other features may be more readily identifiable in a CT image. For example, certain anatomical structures may be more readily identifiable in an MR image than in a CT image, while the reverse may be true of an implanted leadwire. It may therefore be required to correctly register to each other two or more images, e.g., of different imaging modalities, in order to correctly position the various features relative to each other.

Medical images, e.g., of two (or more) different modalities, e.g., MR, CT, DTI, PET, Fluoroscopy, two different MR types (T1 MR and T2 MR), or two different images of the same modality taken at different times etc., may be displayed overlaying each other. In an example embodiment, a user-interactive sliding scale may be provided, where a control may be shifted between first and second edges of a slide bar, where the first edge corresponds to one of the images, and the second edge corresponds to the other image. The closer the user shifts the control towards the first edge, the more of first image is represented in the merged display and the less of the second image is represented in the merged display. The closer the user shifts the control towards the second edge, the more of second image is represented in the merged display and the less of the first image is represented in the merged display. For example, at a left edge, only the MR would be shown, at the right edge, only the CT would be shown, and at a center point, both images would be equally represented.

In an example embodiment of the present invention, the system may provide a selectable option for presenting the two images in a checkerboard pattern including a plurality of image blocks, where for each pair of adjacent ones of the plurality of image blocks, a portion of the first image is revealed in one of the blocks of the pair and a portion of the second image is revealed in the other of the blocks of the pair, as though the portion of the first image displayed in the one block obstructs the view of the portion of the second image that is adjacent the portion of the second image that is displayed in the other of the blocks of the pair, that would have otherwise been displayed.

In an example embodiment, a user interface pivot and stem tool may be provided via interaction with which the user may change the alignment of the images relative to each other.

Figure 2:
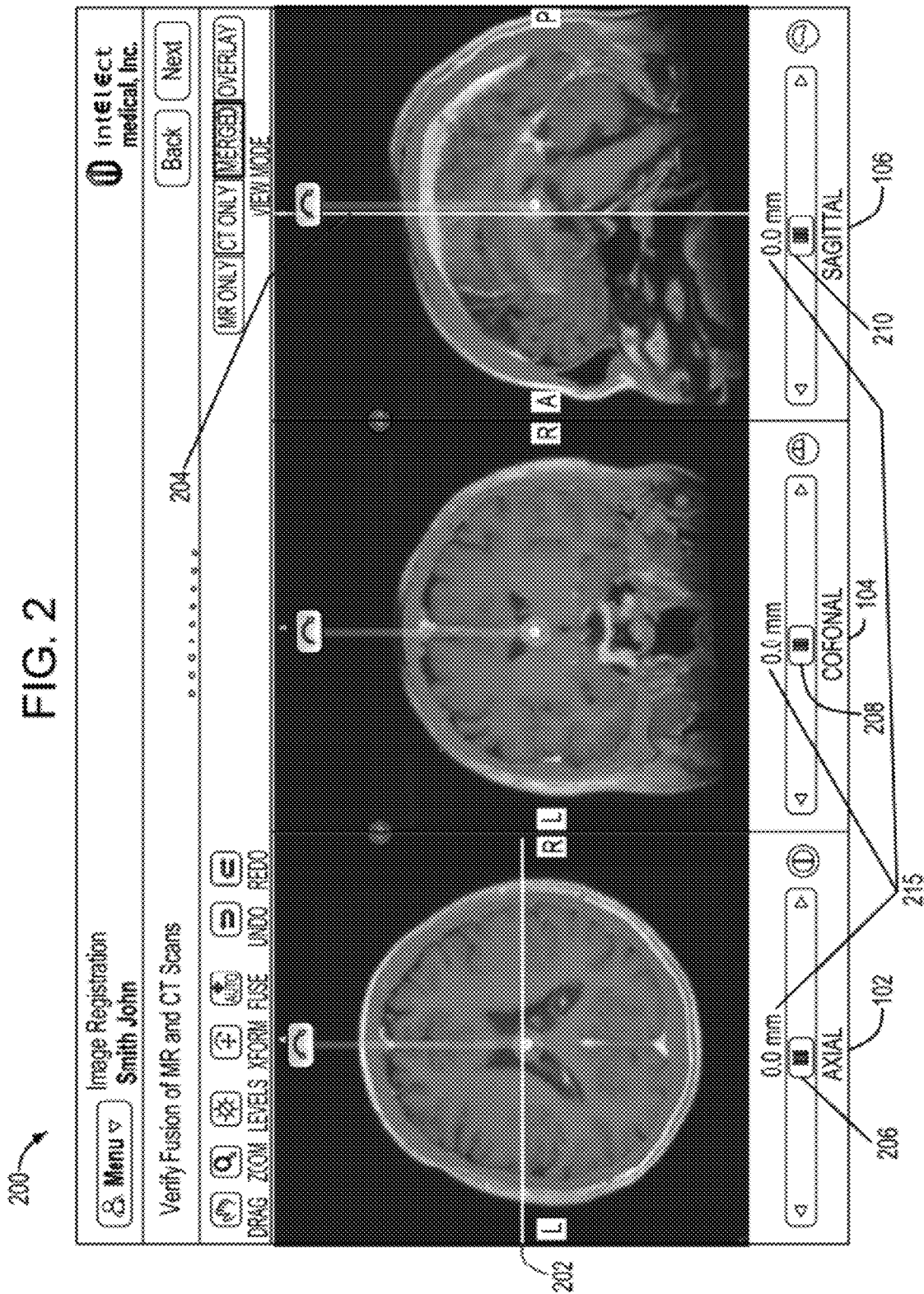
FIG. 2 is a screen shot showing markers for illustrating cross-section relationships between orthogonal image slices, according to an example embodiment of the present invention.

A screen may be divided into 3 panes to show the overlaid images in, respectively, the axial, coronal, and sagittal views, as shown in FIG. 1. In alternative example embodiments, a screen may be divided into further panes to show additional views. FIG. 1 shows an example screen shot 100 of a user interface including an axial pane 102, a coronal pane 104, and a sagittal pane 106. In an example embodiment of the present invention, when the user interacts with a tool for modifying the registration of the overlaid images to each other in one of the panes, the system displays a cross-section indicator, e.g., in the form of a line, in each of the other two panes at a location of which the image, in the active pane in which the user is modifying the registration, is a cross-section. For example, the user may be modifying registration of axial images, which correspond to a cross-section view of a particular point in the coronal and sagittal images of the other two panes. Such information conveyed by the cross-section indicator is useful to the user to identify what is being viewed in the active pane by providing the user visual information regarding the surroundings of the slice to which the user is navigating in the active pane. FIG. 2 shows an example screen shot 200, where the coronal pane 104 is active and cross-section indicators 202 and 204 are displayed, respectively, in axial pane 102 and sagittal pane 106.

In an alternative example embodiment, the line in the non-active panes showing the correspondence to the display in the active pane may be displayed in response to interaction with a user interface control for changing the viewed image slice in the active pane, and is removed in response to release of the control. For example, FIG. 2 shows an axial image slice navigator slider control 206 for navigating between different axial slices, a coronal image slice navigator slider control 208 for navigating between different coronal slices, and a sagittal image slice navigator slider control 210 for navigating between different sagittal slices. The user may select one of the slider controls 206, 208, 210, and slide the respective control to change the viewed image slice in the respective view. Alternatively, the user may select a control button located at a far edge of a bar along which the slider control is slidable (e.g., a left pointing arrow and a right pointing arrow), in response to which selection the system may correspondingly continuously slide the slider control toward the selected control button until the user releases the control button.

For each displayed image slice, the system may, in each pane, identify, e.g., immediately above a slider bar in which the slider control is slidable as shown in FIG. 2, a distance the anatomical portion to which the displayed image corresponds is from a predetermined origin coordinate. For example, a point that approximates the center of the brain may be used by the system as the origin. When the user manipulates one of the slider controls to change the viewed slice in a respective active pane, the system may update a distance identification 215 of the active pane to reflect the distance of the anatomical region corresponding to the newly displayed image slice from the origin. For example, should the user slide the slider control 208 of the sagittal pane to the right, the system may modify the distance identification 215 in the sagittal pane to indicate a positive number of millimeters, and, should the user slide the slider control 208 of the sagittal pane to the left, the system may modify the distance identification 215 in the sagittal pane to indicate a negative number of millimeters. Accordingly, upon selection of any of the slider controls 206, 208, 210 in a respective one of the panes, the system may display the cross-section indicators in the remaining panes, and upon release of the selected slider control, may remove the cross-section indicators from those remaining panes.

The user may perform the registration modifications in any of the 3 panes 102, 104, 106. Indeed, the user may switch between all of the 3 panes to perform parts of the registration modification.

One of the tools the user may use to modify the image registration is a pivot and stem tool 110, which may be displayed in each of the panes 102, 104, 106. For example, the system may display the pivot and stem tool 110 in response to selection of a graphical input object, such as a button in a toolbar, shown in FIG. 1 as "xform" graphical button 115, which may be displayed in a tool bar. The pivot and stem tool 110 may include a stem associated by the system with one of the two images to be registered. For example, FIG. 1 shows an overlaid CT image and MR image. The stem may be associated with the CT image or the MR image. In an example embodiment, the system may be configured to receive user-input selecting with which of the two images the stem is to be associated. The stem may extend from a center of the associated image and/or a center of a significant object within the image. For example, the user may place the first stem edge of the stem at a point within the image which the user perceives as being the center of the object. Alternatively, the system may automatically detect the significant object and place the first stem edge at the center of the detected significant object. For example, the image may be a CT of a patient's brain, in which an area of the image corresponding to matter as dense as the skull or denser is saturated, i.e., the upper limit of used pixel values is used for all such matter. The system may detect where such values lie in the image and match a formed structure to that which corresponds most closely to a template of a skull, thereby setting such structure as the significant object at the center of which to set the first edge of the stem. Alternatively, the system may automatically place the stem edge at the center of the image. The stem may extend from the first edge at the center and outwards to a second stem edge.

In an example embodiment, the user may select the first edge associated with the center and drag it, in response to which the system translationally shifts the associated image relative to the underlying image. For example, the user may move a pointer to the first edge using any suitably appropriate input device, such as a computer mouse, and select it, e.g., via a click or via a different input, such as via a keyboard, and drag it, e.g., by correspondingly dragging the computer mouse or another input device. A stylus or even a finger may instead be used, e.g., where touch-screen functionality is provided. Any suitably appropriate input device or combinations thereof usable for a point-click-drag operation may be used.

In an alternative example embodiment, in response to shifting the first edge, the center of rotation (as described below) may be shifted relative to the image that is rotated via interaction with the pivot and stem tool. According to this embodiment, the system may provide for shifting one of the images relative to the other by user selection of any point of the displayed images (e.g., other than the interactive elements of the pivot and stem tool) and a subsequent drag. For example, the system may associate the selection with one of the images, and, in response to the drag while the image is selected, the system may shift the associated image relative to the other image.

The user may also select the second edge and drag it to the right or the left of the stem, in response to which the system may rotate the associated image relative to the underlying image. For example, if the user drags the second stem edge to the right, the system may rotate the associated image clockwise, while, if the user drags the second stem edge to the left, the system may rotate the associated image counter-clockwise. For example, FIG. 2 shows the stem control 110 in axial pane 102 after a clockwise shift of the stem control 110 or shift to the right of the stem control 110 in the axial pane 102, and correspondingly shows the clockwise rotation of the MR image relative to the CT image in the axial pane 102. It is noted that in response to a rotational and/or translational shift of one of the images relative to the other in one of the panes, the mages in the other panes may be correspondingly changed.

The user may also select the second edge and drag it in-line with the stem inwards towards the first edge or outwards further away from the first edge, in response to which the system may correspondingly shorten or lengthen the stem. The length of the stem may impact the rotational shift of the associated image in response to subsequent dragging of the second edge to the right or left. For example, the longer the stem, the less the rotational shift of the image in response to the left or right drag because, the further from the center of the rotation, the greater the distance that must be covered for a particular angular change. The user may therefore desire to work with a longer stem for a precise rotational shift, or a shorter stem for a quick rotational shift.

It is noted that the image with which the stem is associated may be the underlying image and the stationary image the overlying image, or vice versa.

Overlay Controls for an Overlay View Mode During Registration

As noted above, DTI, PET, Fluoroscopy, two different MR types (T1 MR and T2 MR), etc., may be co-registered. In an example embodiment of the present invention, the system may display a flashlight bar 315, as shown in screen shot 300 of FIG. 3, above the images in each of the panes 102, 104, 106. With respect to each respective one of the panes 102, 104, 106, a first one of the images may be displayed in the viewing pane except at a section extending downwards from the bar 315, e.g., along an entire or approximately an entire length of the bar 315, at which section the second of the images is displayed. The bar 315 may therefore function as a flashlight for shining onto the second image, allowing it to come into view under the bar 315. While the bar 315 is described as being at the top of the pane and shining downwards, the bar 315 may similarly be positioned instead at the bottom of the pane and shine upwards or may be positioned at one of the right and left sides of the pane and shine towards the opposite side.

The user may select the bar 315 and drag it, for example, using any suitably appropriate input device that provides a point-click-drag functionality. In response to such user input, the system may correspondingly shift the bar 315. For example, where the bar 315 is positioned at the top of the pane, the system may shift the bar 315 to the right or left. The images may remain stationary with respect to their positions relative to each other and an area corresponding to the entirety of the images may remain fixed relative to the display pane while the bar 315 shifts. The region of the second image on which the bar 315 shines for bringing the respective region into view, however, may correspondingly shift in response to the shifting of the bar. For example, while the bar 315 is at a center position of the pane, a region of the second image that is at the center of the pane may come into view, and when the bar 315 is shifted to the right, the center region (or a portion of the center region) may move out of view while a region to the right, not previously in view, correspondingly comes into view. The bars 315 in each pane may be independently operated.

Figure 3:
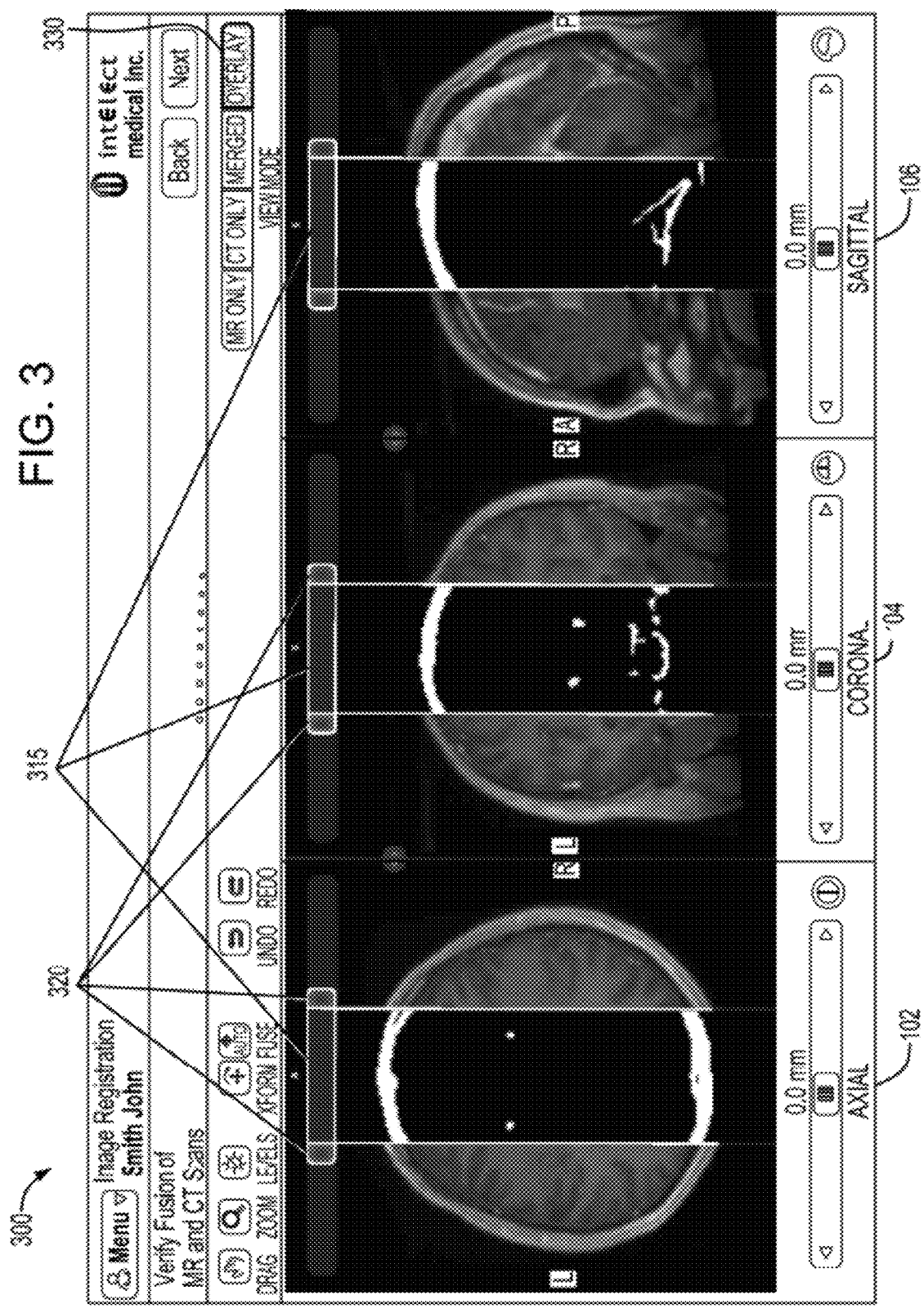
FIG. 3 is a screen shot showing a flashlight tool for showing regions of an image, according to an example embodiment of the present invention.

For example, in FIG. 3, the image portions displayed in the regions corresponding to the bars 315 of panes 102, 104, 106 are of CT images, while remaining image regions of the panes show portions of MR images.

The bars may also include a respective bar sizing control 320 at each edge of the bar, which the user may select and drag, e.g., using any suitably appropriate input device providing point-click-drag functionality (or any other suitable input device), to lengthen or shorten the respective bar 315, and the corresponding region of the second image which is shown. For example, if the bar 315 is placed at the top of the pane, the bar sizing control 320 at the right edge may be selected and dragged either right to lengthen the bar 315 or left to shorten the bar 315; and the bar sizing control 320 at the left edge may be selected and dragged either to the right to shorten the bar 315 or to the left to lengthen the bar 315.

Figure 27:
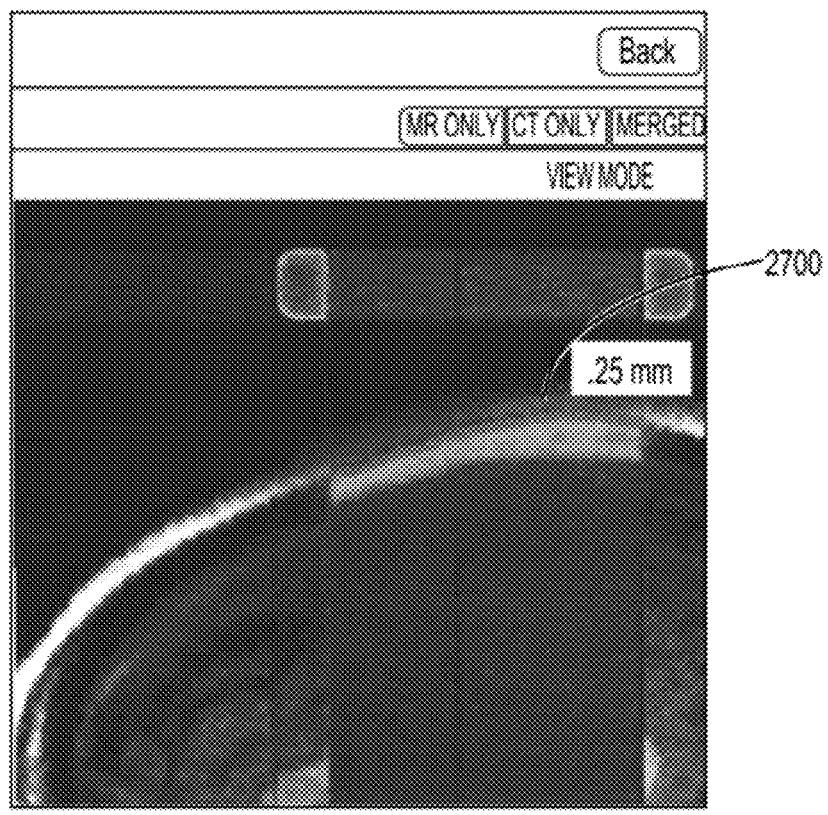
FIG. 27 is a screen shot showing a highlighting of an anatomically significant portion of a flashlight region, according to an example embodiment of the present invention.

In an example embodiment of the present invention, the system may highlight regions within the section of the display corresponding to the flashlight bar 315 predefined as significant anatomical regions. For example, FIG. 27 shows a highlight region 2700, in which a skull line in a CT image is highlighted, which may help the user determine how well the two images are aligned.

In an example embodiment of the present invention, the system may display the bar 315 and associated bas sizing controls 320, and the associated views of the images, in response to selection of a graphical input object, such as a button in a toolbar, shown in FIG. 3 as "overlay" graphical button 330, which may be displayed in a tool bar.

In an example embodiment, the bar 315 and associated controls 320 and image views may be provided in combination with the pivot and stem control 110. For example, if the user selects the "xform" button 115 while in the overlay mode entered into in response to the selection of the "overlay" button 330, the pivot and stem control 110 may be displayed and operated in the overlay mode.

Drag and Drop Marker Placement

In an example embodiment of the present invention, the system may be configured to record structural information regarding anatomical structures represented in the medical images. The system may then use the recorded anatomical structure information concerning the images for registering other anatomically related objects to the medical images. For example, an anatomical atlas or other volumes, such as those of a DTI atlas or other medical images obtained from a patient population may be registered to the patient's medical images in accordance with the recorded anatomical structure information.

In an example embodiment of the present invention, the system may provide a user interface via which a user may provide input identifying certain anatomical landmarks usable by the system for performing such later registration to other anatomically related objects. For example, the other anatomically related objects may be warped to represent an anatomical structure whose corresponding landmarks are positioned in a manner that corresponds to the positioning of the landmarks identified by the user, as described in further detail below.

In an example embodiment of the present invention, a marker may be associated by the system with such predefined landmarks. For example, a marker may be associated by the system with the anterior commissure (AC) and another marker may be associated by the system with the posterior commissure (PC). While the discussion below refers to the AC and PC, the described features may be applied to other predefined, e.g., anatomically significant, landmarks. The markers may be displayed differently in the displays so that the user can identify one of the markers as being associated with the AC and the other as being associated with the PC. For example, the system may label one of the markers "AC" and the other marker "PC" and/or the markers may be displayed using different shapes or colors (or may be visually distinguished in another suitably appropriate manner). For example the AC marker may be orange and the PC marker may be blue.

The markers may be selectable and draggable. The user may select each of the markers and place it in a displayed MR image, for example, in any one of the three panes corresponding to the axial, coronal, and sagittal views. In response, the system may also display AC and PC markers in the other two panes at positions corresponding to the user placement of the markers in the first pane.

Figure 4:
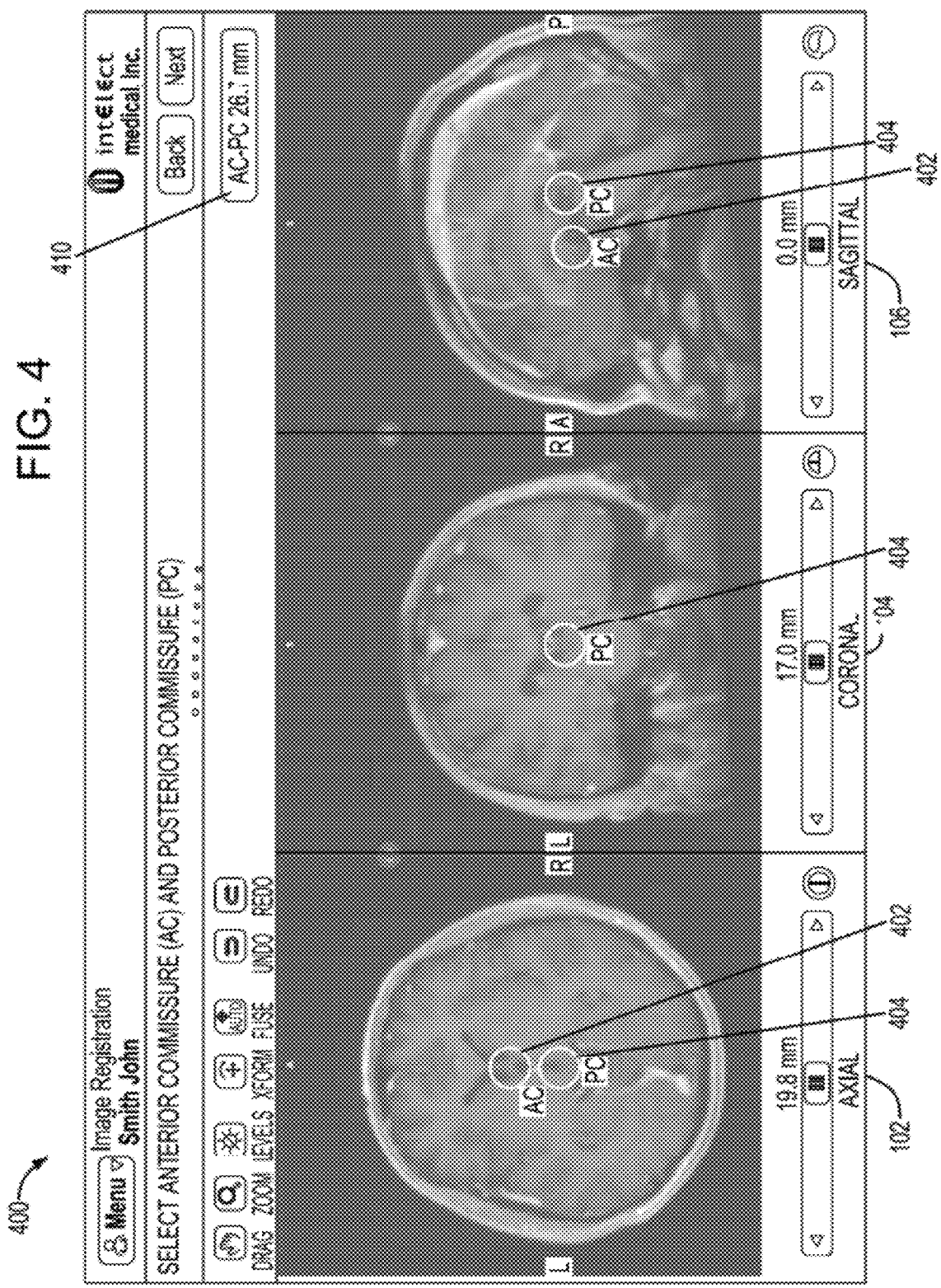
FIG. 4 is a screen shot of a user interface via which to mark an anterior commissure (AC) and posterior commissure (PC), according to an example embodiment of the present invention.

FIG. 4 shows an example screen shot 400 in which an AC marker 402 and a PC marker 404 are displayed in those of panes 102, 104, 106 displaying image slices of anatomical regions to which the user anchored the respective markers 402 and 404. For example, the markers 402 and 404 may represent a three-dimensional volume. In response to positioning, by the user, of one of the markers at a particular position in one of the image panes, the system may automatically anchor a corresponding marker representing a cross section of the three dimensional volume, that is orthogonal to the cross section represented by the user-placed marker, in each of the remaining views displaying an image slice including a region corresponding to a portion of the three dimensional volume to which the placed marker corresponds. Alternatively, a user-selectable control, e.g., a button or icon, may be displayed, in response to which selection, the system displays the corresponding markers in the other views according to the marker set by the user in one of the views.

In an example embodiment of the present invention, each of the panes 102, 104, 106 may include a control 206, 208, 210, as described above with respect to FIG. 2, for scrolling through image slices of the corresponding pane. If the user places a marker, e.g., the AC marker 402, in a displayed axial image slice in one of the panes, the system may automatically place a corresponding marker, e.g., another AC marker 402, in each of the displayed sagittal and coronal panes at a position that corresponds to the displayed axial slice in which the user dropped the AC marker 402, as long as the images displayed in the sagittal and coronal panes 104, 106 includes a region corresponding to the axial region in which the user placed the AC marker 402.

Referring, for example, to FIG. 4, if the user places the PC marker 404 at the position shown in axial pane 102, the system may responsively display the PC marker 404 in each of the coronal and sagittal panes 104 and 106 shown in FIG. 4, because the image slices displayed in panes 104 and 106 are cross sections of the axial slice displayed in pane 102, which cut through the anchored PC marker 404. On the other hand, if the user places the AC marker 402 at the position shown in axial pane 102, the system may responsively display the AC marker 402 in the sagittal panes 106 shown in FIG. 4, because the image slice displayed in pane 106 is a cross section of the axial slice displayed in pane 102, which cuts through the anchored AC marker 402; but may omit responsive display of the AC marker 402 in the coronal pane 104 shown in FIG. 4, because the image slice displayed in pane 104 is a cross section of the axial slice displayed in pane 102, which does not cut through the anchored AC marker 402.

While the above has been described with respect to interaction by the user with the axial pane 102, the same would apply if the user instead interacted with either of the panes 104, 106 for placement of the AC marker 402 or PC marker 404 therein, in which case the system would correspondingly update the remaining two panes to include a corresponding marker, where appropriate.

Similarly, in response to a user shift of either of the markers to the right or left in the axial pane 102, the system may correspondingly shift the corresponding marker in the coronal view to the right or left. The position of the corresponding marker within the sagittal pane 106 may be left unchanged, although it may be removed from view or may come into view in the sagittal pane 106 in response to the shift of the marker in the axial pane 102, depending on whether the new position correspond to a region represented in the displayed image slice of the sagittal pane 106. The same would be true if the user shifted the marker to the right or left in the coronal pane 104. Alternatively, in response to the shift of the marker in the axial or coronal panes 102, 104, the system may scroll through slices in the sagittal pane 106 so that a slice including a region corresponding to the new position of the marker is displayed.

Similarly, if the user shifts a marker anteriorly or posteriorly in the sagittal pane 106, the system may correspondingly remove from view or bring into view the corresponding marker in the coronal pane 104 according to the first described embodiment or may correspondingly scroll image slices in the coronal pane 104 according to the second embodiment. Similarly, if the user shifts a marker superiorly or inferiorly in the sagittal pane 106, the system may correspondingly remove from view or bring into view the corresponding marker in the axial pane 102 according to the first described embodiment or may correspondingly scroll image slices in the axial pane 102 according to the second embodiment. Similar steps would be performed when shifting markers in any of the panes, to correspondingly modify the remaining two panes.

As noted above, according to an example embodiment, if the user shifts a marker in one of the panes from a first position to a second position, the first position having a corresponding position in a displayed image slice in another of the panes, but the second position not having a corresponding position in the same image slice of the other pane in which the position corresponding to the first position is located, the system may scroll the image slices in the second view to one in which a position corresponding to the second position is located.

For example, if, in the axial pane 102, the user shifts the AC marker 402 to an image slice of a more anterior portion of the brain, the system may accordingly scroll through image slices of the coronal pane 104 to one corresponding to a cross section at the more anterior portion of the brain and may display the AC marker 402 in the new position in the newly displayed coronal image slice. The same would be true of the PC marker 404 if the user shifted the PC marker 404 in one of the views. However, while the scrolling may be performed so that the marker being shifted is in view in each of the panes 102, 104, 106, the scrolling may cause the non-manipulated marker to move out of view in one of the panes.

The system may calculate the distance between the points of the brain marked by the user placed AC and PC markers, and may display the calculated distance. For example, FIG. 4 shows a displayed AC-PC distance identifier 410. As the user shifts the markers, the system may update the displayed distance.

After placement of a marker, the user may directly scroll to other image slices of any of the views, e.g., using the slider controls 206, 208, 210. In each of the views, the system may display the markers with the greatest brightness in the respective slices in which the markers were anchored. As the user scrolls to other slices in which the marker was not anchored, the marker may be gradually dimmed until it is no longer visible. Therefore, the user may be able to determine from the brightness of the markers, with respect to each of the panes 102, 104, 106 whether the AC/PC is in the displayed slice, in a slice that is near to the displayed slice, or in a slice that is not near to the displayed slice.

In an example embodiment of the present invention, the system may display on the slice scroll bar markers that correspond to the AC and/or PC, at positions of the slice scroll bar that correspond to the image slices to which the user-placed AC/PC markers have been anchored. For example, where an orange user-placed marker is used for anchoring the position of the AC, the system may display an orange, e.g., vertical, line at a location of the slice scroll bar corresponding to the image slice to which the AC has been anchored. Similarly, where a blue user-placed marker is used for anchoring the position of the PC, the system may display a blue, e.g., vertical, line at a location of the slice scroll bar corresponding to the image slice to which the PC has been anchored.

In an example embodiment of the present invention, the system may display selectable buttons or icon corresponding to the AC and to the PC, in response to selection of which, the system scrolls to the image slice corresponding to the selected button or icon in the active pane or, alternatively, in all of the panes.

The system may provide a zoom tool for carefully analyzing the AC/PC position as set by the placement of the AC/PC marker. In an example embodiment, the zoom tool may also be used for fine tuning the placement of the marker. In an example embodiment, the user interface may include a graphical input object, such as a button in a toolbar, for opening the zoom tool. For example, in response to selection of the zoom tool button, the system may open the zoom tool in association with the last active one of the AC marker 402 and PC marker 404. Alternatively or additionally, the system may be configured to display the zoom tool in response to a predefined type of interaction with, e.g., a double-click of, either of the markers. For example, if the user double-clicks the AC marker 402, e.g., using any suitably appropriate input device, the system may responsively display the zoom tool in association with the AC marker 402. Similarly, if the user double-clicks the PC marker 404, the system may responsively display the zoom tool in association with the PC maker 404.

For example, when the zoom tool is selected in one of the panes, the system may zoom in the portion of the image of that pane at which the marker is placed. For example, the marker may be displayed over a portion of an image of the brain. Upon selection of the zoom tool, a portion of the brain image in a region at which the marker was placed may be zoomed in, while a remaining portion of the image remains at the prior zoom setting. The region zoomed may be a predetermined area measured by pixel number, extending about a center of the AC/PC marker. For example, the AC/PC markers, when in a non-zoomed mode, may cover an area of $1,809^2$ pixels (a radius of 24 pixels). When the zoom tool is selected, the system may be configured to zoom in on an area of $7,854^2$ pixels (a radius of 50 pixels) centered about the center of the initial area of $1,809^2$ pixels, so that those are displayed over $31,400^2$ pixels (a radius of 100 pixels). It is noted that the anatomical region covered by the initially placed marker may be smaller or larger than the anatomical region covered in a magnification window of the zoom tool. In an example embodiment, in response to selection of the zoom tool in one of the panes, the size of the marker shown in the remaining panes increases or decreases to indicate the anatomical region covered by the three-dimensional volume of the marker in the magnification window of the pane in which the zoom tool was selected.

Figure 5:
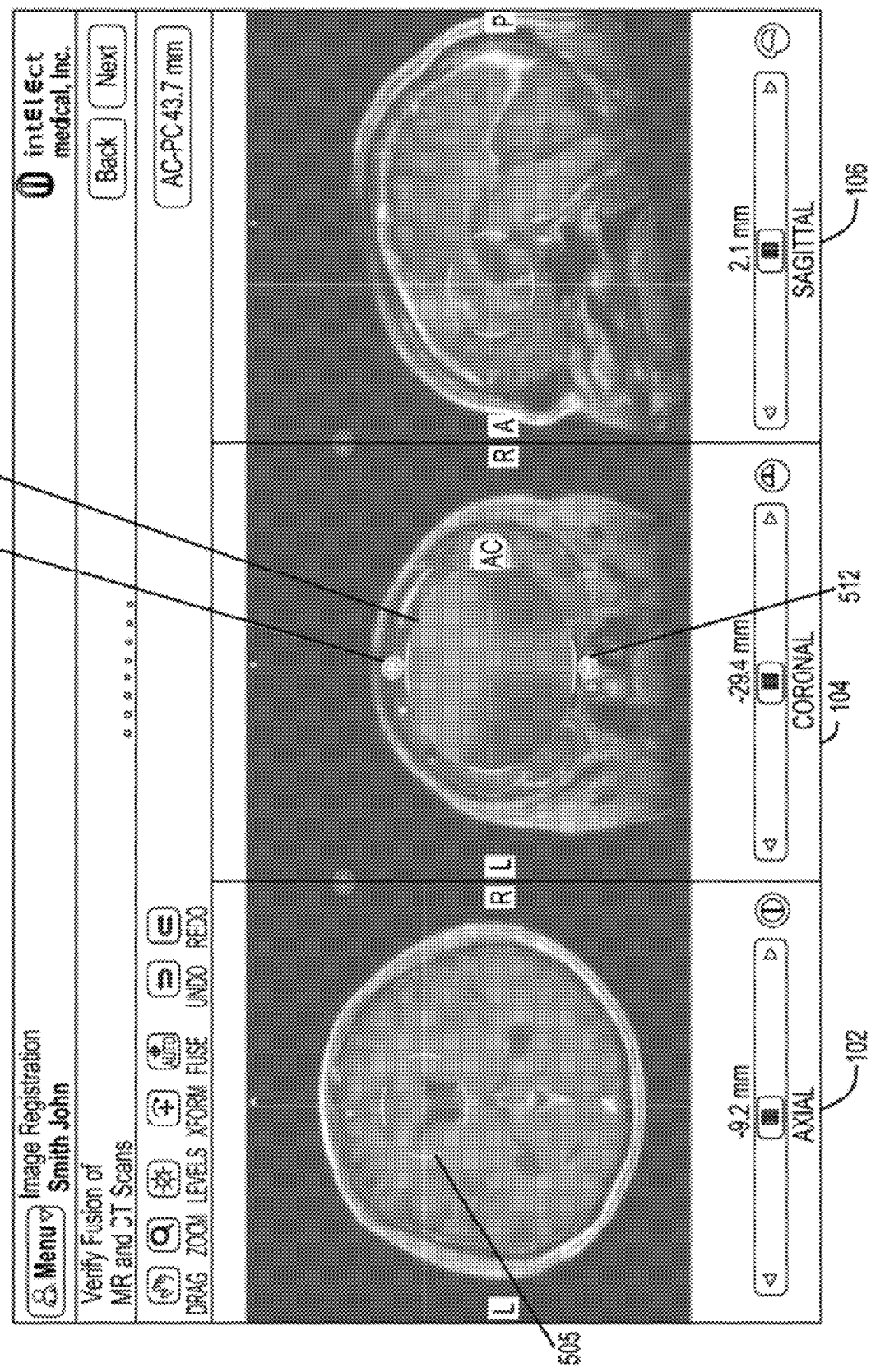
FIG. 5 is a screen shot showing a magnification tool, according to an example embodiment of the present invention.

FIG. 5 shown a screen shot 500 according to an example embodiment of the present invention, in which a magnification window 502 is displayed in coronal pane 104 after selection of the zoom tool while the coronal pane was active, e.g., by double-click of the AC marker 402 in the coronal pane 104. While the a region of the image is magnified in the magnification window 502, the remaining portions of the image remain at the prior zoom setting, with the magnification window 502 overlaying the remaining portions of the image, i.e., being positioned within some of the remaining portions of the image while obstructing others of the remaining portions of the image.

While the magnification window 502 corresponding to the AC is displayed in coronal pane 104, large AC markers 505 are displayed in the axial pane 102 and sagittal pane 106, e.g., corresponding to the size of the three dimensional volume represented by the magnified portion within the magnification window 502.

In an example embodiment, the zoom tool is selected by double-clicking the AC/PC marker. In an example embodiment, after selection of the zoom tool, the portion of the image in the region at which the maker was placed may be returned to the zoom setting of the rest of the image by clicking in the pane or in any of the other panes at a location that does not fall within the zoomed in region. According to an alternative example embodiment, a button, e.g., a GUI button, may be provided, in response to selection of which the system removes the magnification window 502 and the corresponding markers in the other panes, and returns to display of the AC/PC markers that were displayed prior to display of the magnification window 502.

The zoom control may further include sub-controls for increasing or decreasing the zoom of the zoomed in region by predetermined amounts. For example, a '+' may be displayed which is selectable for increasing zoom and a '−' may be displayed which is selectable for decreasing zoom. For example, the zoom tool shown in FIG. 5 includes a zoom increase control 510 displaying '+' to indicate its use for increasing zoom, and is displayed joined to the magnification window 502 at the top of the magnification window 502. The zoom tool shown in FIG. 5 also includes a zoom decrease control 512 displaying '−' to indicate its use for decreasing zoom, and is displayed joined to the magnification window 502 at the bottom of the magnification window 512. Each selection of the zoom increase control 510 or zoom decrease control 512 causes the system to respond by respectively increasing or decreasing the magnification. In an example embodiment, the system may be configured with a limit for zoom increase and/or decrease.

In an example embodiment of the present invention, in response to each operation of the zoom increase control 510 and in response to each operation of the zoom decrease control 512, the system may correspondingly modify the size of the corresponding markers 505 in the other two panes to reflect the modification of the region reflected in the magnification window 502. Alternatively, the system may be configured to leave the markers 505 at their original size set in response to the initial activation of the zoom tool.

While the portion of the image in the region corresponding to the marker is zoomed, the user may click and drag the magnification window 502, in response to which the magnification window 502 and the placement of the anchoring of the corresponding anatomic object (AC or PC) may be correspondingly shifted. Thus, the user is able to shift the recorded placement of the AC or PC while the region is zoomed, which may help the user select appropriate placement of the marker. After deselecting the zoom tool, the corresponding AC marker 402 or PC marker 404 having the same zoom setting as the remaining portions of the image may be displayed at the new location set by the shift of the magnification window 502.

As noted above, a slider control 206, 208, 210 may be operated for scrolling through slices of a respective one of the panes 102, 104, 106. As described above, in an example embodiment, in response to such scrolling in a mode in which the AC marker 402 and PC marker 404 may be set and are displayable (assuming the image slice to which they are anchored is displayed), the AC marker 402 and/or PC marker 404 may fade in and out of display. In an example embodiment, although scrolling from a first image slice to a second image slice may cause the AC marker 402 and/or PC marker 404 to fade from display, if the user operates an image slice scrolling control, e.g., the slider control 206, 208, or 210, to scroll through image slices of a pane while the magnification window 502 is displayed, the system moves the magnification window 502 and the anchoring of the respective anatomical object to the image slice to which the user scrolls. Alternatively or additionally, further controls may be attached to the magnification window 502 for scrolling. For example, buttons similar to controls 510 and 512 may be displayed, where selection of a first one of the buttons causes scrolling of the slices in one direction and selection of a second one of the buttons causes scrolling of the slices in the opposite direction.

Thus, the magnification window 502 may remain in view in a single display position, while the image slices being displayed are scrolled. On the other hand, as described above, if the user operates the image scroll control to scroll through the image slices while the marker region is not zoomed, the anchoring of the anatomical component (AC or PC) of the last-active one of the markers (AC marker 402 or PC marker 404) remains in the prior image slice, and the image slices are scrolled while the corresponding marker fades away with increasing distance between the scrolled-to image slice and the slice in which the corresponding marker was set.

Thus, according to an example embodiment of the present invention, the system may provide two distinct methods by which to shift the AC marker 402 or PC marker 404 between image slices. According to a first method, the system may scroll to different image slices in one of the panes 102, 104, 106 while the magnification window 502 corresponding to the relevant one of the markers is displayed in the respective pane in which the image slice scrolling control is operated. According to a second method, the user may shift the marker in one of the panes to a different slice by shifting placement of the relevant marker in another one of the panes, when the magnification window 502 is not displayed. For example, if the user shifts the AC marker 402 superiorly or inferiorly in the coronal pane 104 or sagittal pane 106, the system may shift the anchoring of the AC (and the display of the AC marker 402) to a different axial image slice. Similarly, an anterior or posterior shift in the axial pane 102 or sagittal pane 106 causes a shift to a different coronal slice. Similarly, a shift to the right or left in the axial pane 102 or coronal pane 104 causes a shift to a different sagittal slice.

The magnification window 502 may be round as shown in FIG. 5, but may be any other suitable shape in alternative embodiments. As shown in FIG. 5, in an example embodiment, the magnification window 502 may include cross-hairs via which to easily identify the portion of the image that lies at the center of the marker, to further help the user correctly place the marker.

In an example embodiment of the present invention, the system may execute an image enhancement algorithm on a zoomed in region. For example, the image enhancement may be applied to the region displayed within the magnification window 502. The image enhancement may include applying one or more image filters to sharpen edges, to facilitate identification of boundaries and structures. In an example embodiment, the image enhancement may be performed automatically, in response to opening of the magnification window 502 and/or for further zooming within the magnification window 502. Alternatively or additionally, one or more image processing filters may be user selectable for application to the zoomed in region. In an example embodiment, the system may provide a list of selectable image filters for application to the zoomed in region. For example, a selectable menu option may be provided when the magnification window 502 is open, for opening the list of selectable image filters. In an example embodiment, the system is configured for input of user-generated custom filters, which may then be added to such a list for application to the region within the magnification window 502.

In an example embodiment, the system may output a patient atlas based on the identified AC/PC, as described below. Additionally or alternatively, the system may register the patient's MR image, in which the AC and PC are identified, to another volume, such as a DTI atlas or an MR image of another patient.

After placement of a marker or a shift of the position of the marker, the user may select an "undo" control, in response to which the system may undo the last placement or shift to and reposition the marker at a prior placement. A complete shift that is separately undoable may be an action including a selection, a drag, and a drop, such that the selection of the "undo" control may cause the processor to reposition the marker at the position at which the marker was selected prior to the drag. For repeated selections of the undo control, the system may undo a series of changes to the marker placement. Similarly, after operation of the pivot and stem tool 110, to modify the relative positions of different images, the user may select the "undo" control, in response to which the system may undo the last modification of the relative positions. For repeated selections of the undo control, the system may undo a series of changes to the relative positions. The "Undo" functionality may be provided for marker placements, leadwire placements, and/or alignment and/or scaling of images.

Auto Histogram and Level of CT+MR in Different Screens

In an example embodiment of the present invention, the system may provide for auto-correction of images in order to provide a best view of relevant features in the images. The view of the features may be useful for a user to properly co-register images based on the positions of the features, to verify a previously performed co-registration, to select and/or verify lead tip and shaft placement, to select and/or verify MCP, MSP, AC, PC or other landmark points, and/or to determine how to set stimulation parameters in a stimulation programming environment.

In an example embodiment, the system may implement the auto-correction prior to initial display of the images. Alternatively, the system may initially display the images without the correction and perform the auto-correction in response to a user input instruction to do so. For example, the system may display a graphical button selectable by the user for instructing the system to perform the auto-correction.

In an example embodiment of the present invention, the type of auto-correction performed by the system depends on the imaging modality of the image. For example, the system may auto-correct an MR image using a first imaging correction method and auto-correct a CT image using a second, different, correction method. The different methods may be implemented automatically without user instruction, or may be implemented in response to a single instruction to auto-correct overlaid images.

For example, in response to user operation of a user interface control, the system automatically adjusts greyscale values of the pixels for a best image.

Figure 6:
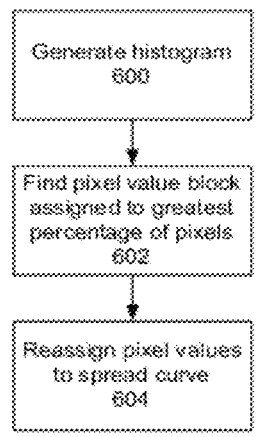
FIG. 6 is a flowchart that illustrates steps for auto-correction for an MR image, according to an example embodiment of the present invention.
Figure 7:
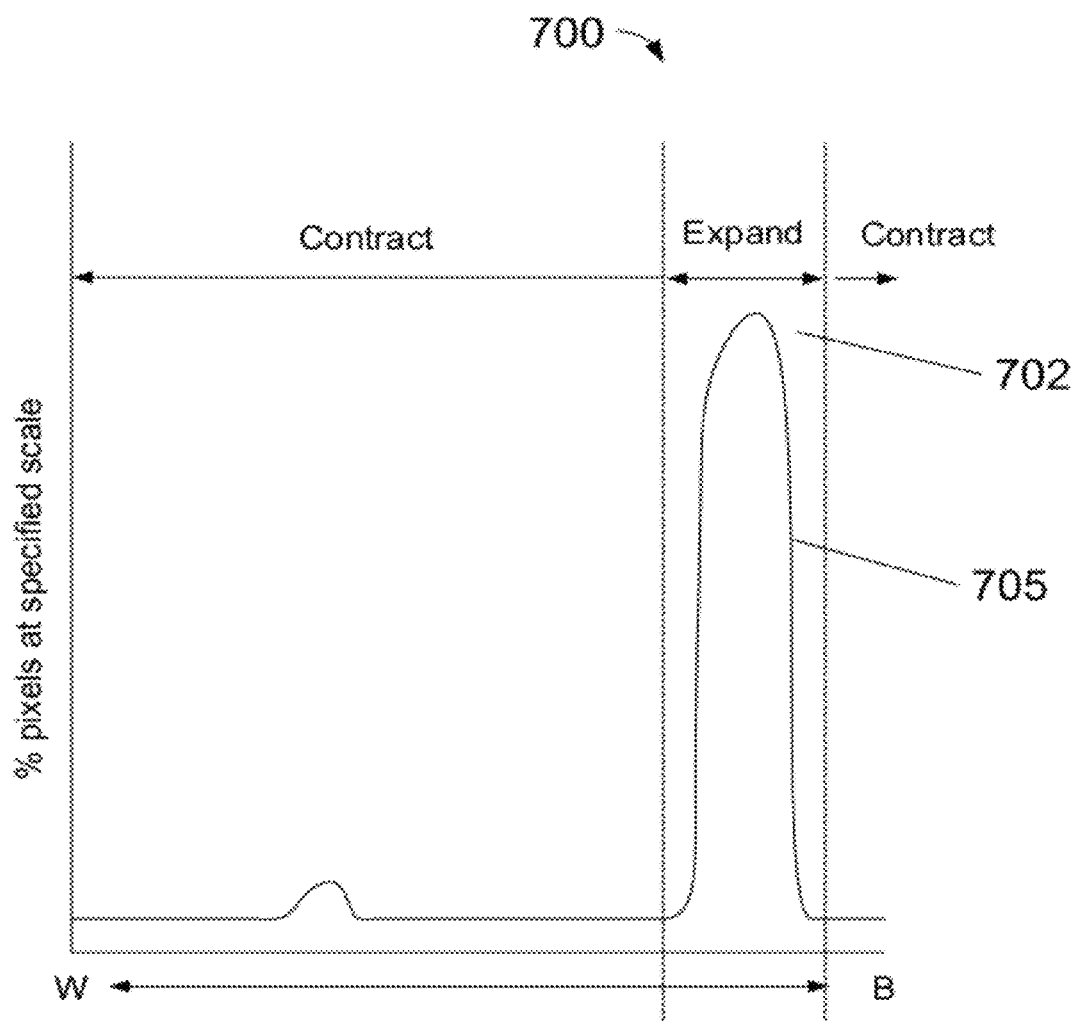
FIG. 7 shows how a histogram may be adjusted in an auto-correction method for correcting an MR image, according to an example embodiment of the present invention.

In an example embodiment of the present invention, the system may automatically enhance an MR image by modifying a distribution of pixel values assigned to the pixels of the image. For example, referring to FIG. 6, the system may, at step 600, generate a histogram based on the greyscale values of the image, which histogram plots the percentage of pixels of the image at various greyscale values, e.g., beginning with white and ending with black, for example, such as histogram 700 shown in FIG. 7. At step 602, the system may identify a region of the graph corresponding to the block of continuous color values having the greatest percentage of pixels. Such a block will usually form a curve, such as curve 705 in block 702 of FIG. 7. The identification of the block may include determining the pixel values at which the curve begins and ends, which pixel values may be set as the outer limits of the block. At step 604, the system may reassign the pixel values to spread that curve out over a greater number of pixel values, so that fewer of the pixels are confined to that range of pixel values than prior to the spread and a greater number of pixels are assigned the pixel values that are external to that range than prior to the spread. Any suitably appropriate histogram equalization method may be used for modifying the assignment of pixel values to the pixels of the MR image.

Such a modification of the MR image causes the MR image to be more clearly show different anatomical features because a greater variety of pixel values are used for showing the different anatomical features.

Figure 8:
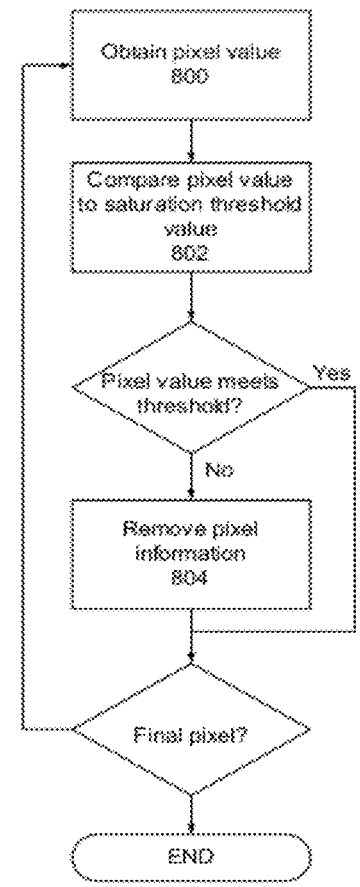
FIG. 8 is a flowchart that illustrates steps for auto-correction of a CT image, according to an example embodiment of the present invention.

As noted above, the system may be configured to differently modify a CT image. What is often relevant in the CT image with respect to stimulation programming is the skull and the leadwire(s). CT images becomes saturated for matter that is as dense as bone or denser, saturation referring to where the CT image no longer differentiates between structures of different density. The system may accordingly be configured to remove all pixel information for those pixels having values other than the saturated level. This would mostly leave the skull and the leadwire(s). For example, FIG. 8 is a flowchart that shows an example method the system may perform for auto-correction of a CT image. At step 800, the system may obtain a pixel value for one of the pixels of the CT image. At step 802, the system may compare the obtained pixel value to a saturation threshold pixel value. If the pixel value does not meet the threshold, indicating that it is not at the saturation level, the system may, at step 804, remove the pixel information. For example, the system may set the value of the pixel to black, e.g., 0. If the pixel value meets the threshold, indicating that it is at the saturation level, the system may skip step 804 for that respective pixel. If the image includes additional pixels not yet so analyzed, the system may return to step 800 for selection of another pixel of the CT image. Otherwise, the method may end.

Other significant structures may be ventricles and sulci, when verifying fusion of and MR and CT. Thus, in an alternative example embodiment, the system is configured to automatically modify the levels of the CT image such that the ventricles and sulci are clearly visible in the CT image.

Thus, the system may be configured to display a images overlaying each other, where the images are auto-corrected via different auto-correction methods in response to the same auto-correct trigger.

Atlas Registration

Identifying a Predefined Plane or Line

In an example embodiment of the present invention, the system is configured to output a graphical representation of a predefined line or plane, e.g., which may be registered to one or more images of an anatomical region. The predefined line or plane may be an anatomically significant line or plane. In an example embodiment, the plane may be the mid-sagittal plane (MSP), a theoretical plane dividing the left and right hemispheres of the brain. The system may store in memory the location of the predefined line or plane, e.g., the MSP, relative to a three-dimensional volume of each of one or more images of one or more imaging modalities. The output representation of the line or plane, e.g., the MSP, may overlay and be relative to the display of one or more of such images in accordance with the recorded relative position. The following discussion will refer to the MSP, but may be applied similarly to other lines or planes.

The graphical representation may be output in a user-interactive interface via which the user may interact with the representation of the MSP and/or with a displayed image over which the MSP representation overlies to modify the location of the MSP relative to the image. The user may interact with the user interface for translating and/or rotating the MSP representation and/or to translate and/or rotate the image, e.g., an MR image, to correctly align the displayed MSP representation with the MR, to coincide with the actual position of the MSP with respect to the anatomical elements as displayed in the MR image.

Figure 9:
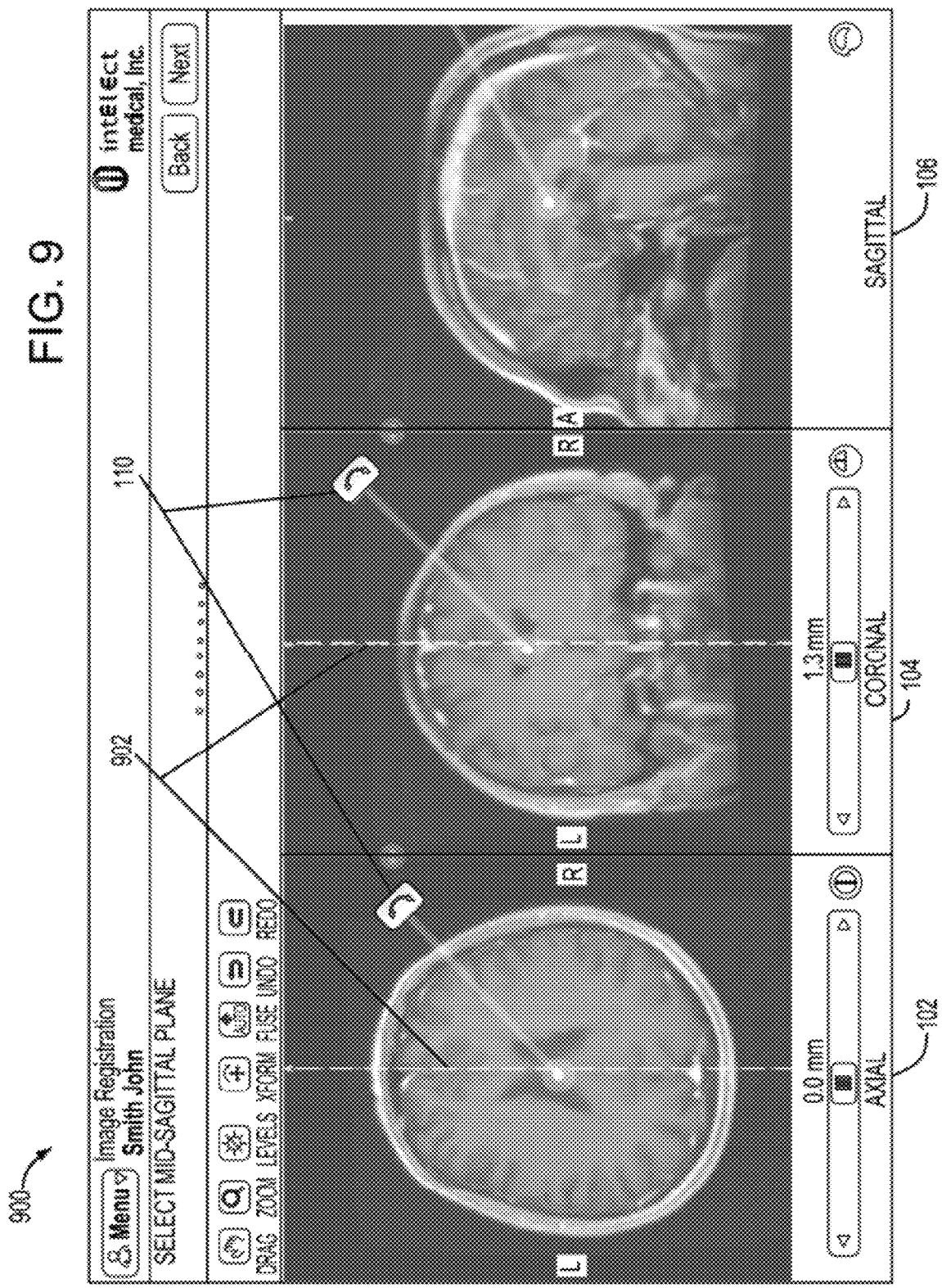
FIG. 9 is a screen shot showing a user interface via which to identify a mid-sagittal plane (MSP), according to an example embodiment of the present invention.

For example, FIG. 9 shows an example screen shot 900 in which a broken line is used as an MSP representation 902. The MSP representation 902 is displayed in each of the axial pane 102 and the coronal pane 104, indicating a cross-section of each of the respective image slices of those panes through which the MSP cuts. In an example embodiment, as shown in FIG. 9, the MSP representation 902 is omitted from sagittal pane 106 because the MSP does not cut through a cross-section of a sagittal image slice. Instead, the MSP is theoretically in line with one of the sagittal image slices, encompassing an entirety of that sagittal image slice.

In an example embodiment of the present invention, and as shown in FIG. 9, the pivot and stem tool 110 may be provided in each of the axial pane 102 and the coronal pane 104 while in a MSP anchoring mode in which the user may interact with the user interface for modifying a relative position of the MSP to the image. The pivot and stem tool 110 may be operated for shifting and rotating respective ones of the images displayed in the axial pane 102 and coronal pane 104. It is noted that in alternative example embodiments, other user input methodologies may be used, for example, for all operations described herein as being performable via interaction with the pivot and stem tool 110. For example, a user may drag the image with a finger or stylus via a touch screen, where a motion tracing an arc is interpreted as a rotation, or where two fingers simultaneously dragging in opposite directions is interpreted as a rotation, and where other simpler left/right/up/down motions are interpreted as translations. Alternatively, the user may click an image and then click directional keyboard buttons or GUI buttons, such as straight and/or curved directional arrows, for translating and/or rotating the image.

Referring again to FIG. 9, in response to a left or right shift of the image in the axial pane 102, thereby oppositely shifting the recorded location of the MSP (and the MSP representation 902) relative to the image of the axial pane 102, the system may correspondingly shift the image displayed in the coronal pane 104 to the left or right, thereby oppositely shifting the record location of the MSP (and the MSP representation 902) relative to the image of the coronal pane 104. Similarly, in response to a left or right shift of the image in the coronal pane 104, thereby oppositely shifting the recorded location of the MSP (and the MSP representation 902) relative to the image of the axial pane 104, the system may correspondingly shift the image displayed in the axial pane 102 to the left or right, thereby oppositely shifting the record location of the MSP (and the MSP representation 902) relative to the image of the axial pane 102.

In response to either the left or right shift of the image in either of the axial pane 102 or coronal pane 104, the system may automatically scroll the image slices in the sagittal pane 106 so that the displayed sagittal image slice is the cross-section of the axial and coronal image slices through which the MSP representations 902 in each of the axial and coronal panes 102, 104 extends.

A left or right shift of the image in the sagittal pane 106 may similarly cause the system to modify the image displayed in the coronal pane 104, because the position of the image in the sagittal pane 106 along the horizontal axis may define the center point of the brain along the line extending between the anterior and posterior extremities of the brain, thereby redefining the origin from which coronal slice distances are measured. If a displayed coronal image slice is indicated to be at the origin (0.0 mm), then, in response to the left or right shift of the image in the sagittal pane, a different image slice at the newly defined origin may be displayed in the coronal plane 104.

Similarly, in response to a shift of the axial image upwards or downwards, the system may modify the image of the coronal pane 104 to reflect the new origin coordinate with respect to the anterior and posterior directions.

Similarly, in response to a shift of the sagittal image slice upwards or downwards, the system may change the image in the axial plane 102 to reflect the new origin coordinate with respect to the superior and inferior directions. The same modification of the axial image slice may be performed in response to an upwards or downwards shift of the coronal image.

A rotation of the image in the axial pane 102 redefines the coordinate of the most anterior and posterior points, and the most left and right points of the image. Since the coronal pane 104 displays image slices that are orthogonal to a line extending between the anterior and posterior extremities and parallel to a line extending between the left and right extremities, therefore, in response to the rotation of the image in the axial pane 102, the system correspondingly changes the image of the coronal pane 104 to be of a slice that is orthogonal to the newly defined line extending between the newly defined anterior and posterior extremities.

Similarly, since the sagittal pane 106 displays image slices that are parallel to a line extending between the anterior and posterior extremities and orthogonal to a line extending between the left and right extremities, therefore, in response to the rotation of the image in the axial pane 102, the system correspondingly changes the image of the sagittal pane 106 to be of a slice that is parallel to the newly defined line extending between the newly defined anterior and posterior extremities.

Similarly, a rotation of the image in the coronal pane 104 redefines the coordinates of the most superior and inferior extremities and left and right extremities. The images displayed in the axial and sagittal panes 102, 106 may therefore be correspondingly changed. Similarly, a rotation of the image in the sagittal pane 106 redefines the coordinates of the most superior and inferior extremities and the most anterior and posterior extremities. The images displayed in the axial and coronal panes 102, 104 may therefore be correspondingly changed.

The above discussion regarding responding to translational or rotational changes to an image in one of the panes with modifications of image slices in other panes applies as well to other modes described herein in which images are translatable and/or rotatable, e.g., a mode in which the alignment of an MR image and a CT image is modifiable and/or a mode in which the AC marker 402 and PC marker 404 can be set.

In an alternative example embodiment, the system is configured for receiving user input for selecting three points in MR slices for definition of a plane with respect to an image, e.g., the MR, that is representative of the MSP. For defining the MSP with respect to all views (axial, coronal, and sagittal) it may be required for the system to receive the input of at least two of the points in different axial slices. This does not require that the selection be within different MR axial slices. Instead, for example, two of the points may be selected in an axial MR image, and a third may be selected in a coronal MR image, where the third point is in a different anatomic axial slice than the that to which the MR axial image slice, in which the first two points were selected, corresponds. It may further be required for the system to receive the input of at least two of the points in different coronal slices. This does not require that the selection be within different MR coronal slices. Instead, for example, two of the points may be selected in an axial MR image, and a third may be selected in a coronal MR image, where the third point is in a different anatomic coronal slice than that to which the MR axial image slice, in which the first two points were selected, corresponds. (Alternatively, two of the points may be selected in the coronal view and the third point may be selected in an axial view at a point that corresponds to a coronal slice different than the one to which the coronal image, in which the first two points were selected, corresponds.)

It is noted that the MSP does not always correspond entirely to a single image slice displayed in the sagittal pane 106. Therefore, the three points cannot be noted entirely in the sagittal view in most instances. Additionally, because the MSP may be angled in two orthogonal directions with respect to a plane corresponding to a sagittal image slice, therefore it may be more practical to select the points in the axial and coronal panes 102, 104 rather than the sagittal pane 106.

In an example embodiment, the system may be configured to provide a user interface where user interaction for defining the MSP is limited to the axial and coronal images, e.g., by translation or rotation of a representation of the MSP or of the images, or by placement of the three points in the images, while locking the sagittal image against such interaction, because of the greater preciseness expected in most instances in defining the MSP in the axial and coronal panes 102, 104 due to common angling of the MSP in the directions orthogonal to the sagittal image.

Figure 10:
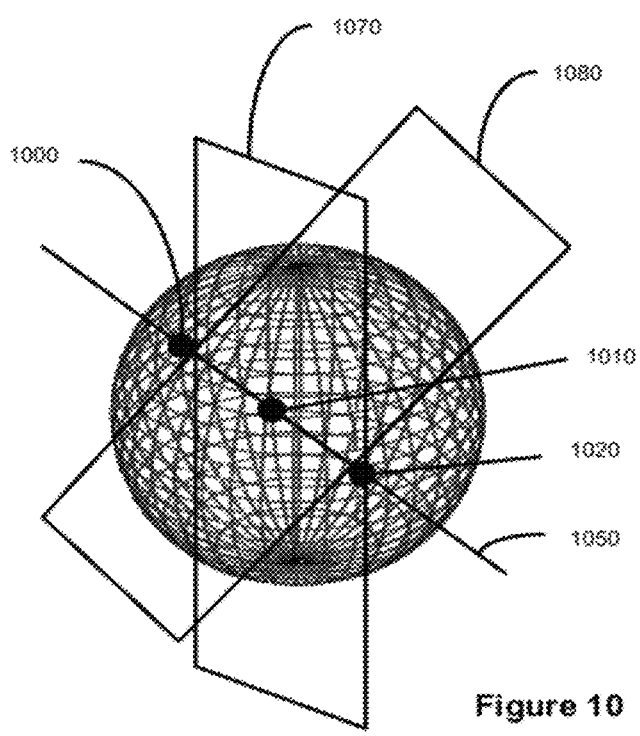
FIG. 10 shows how a line of points may fall within differently angled planes.

Referring to the definition of the MSP by placement of three points, it may be required to receive input of three points in different axial and coronal slices because, otherwise, only a single line would have been defined, and how the plane extends from the defined line to planes parallel to the one in which the line was defined would be unknown. For example, FIG. 10 shows three points 1000, 1010, and 1020 defined along a single line 1050 within a three dimensional space. The line 1050 is included in each of planes 1070 and 1080. However, the planes 1070 and 1080 cross the line 1050 at different angles. Therefore, definition of three points along a single line does not provide enough information to define a plane. For example, if the three dimensional volume of FIG. 10 would represent a brain, and the points 1000, 1010, and 1020 would be defined along a single line in a sagittal image slice, the angle of the MSP plane to the plane defined by the sagittal slice would be unknown.

In an example embodiment, the system may initially receive input identifying the location of the AC and the location of the PC, e.g., as described in detail above, which the system may use as two of the points for defining the MSP. Subsequent to receipt of the AC and PC locations, the system may present a UI in which to select a third point for completion of the definition of the MSP. For example, the user may set the AC and PC points in an axial image slice and set the third point of the MSP in a coronal image slice.

In an example embodiment of the present invention, the system may provide two or more, e.g., all, of the described functionality for aligning multiple images to each other, setting the AC and PC locations, identifying the MSP, modifying a position and/or size of a flashlight bar, and scrolling image slices, in a single GUI presentation. In example embodiments, the system may be configured not to combine various ones of those described features in a single GUI. In an example embodiment, the system may be configured to present certain of the described features in separate GUIs in a defined sequence, which may be followed by inputting "Next" and "Back" commands. For example, the system may be configured to initially present a GUI via which a user may co-align different images. In response to an instruction to proceed to a next step, the system may present a GUI via which to set the MSP. In response to yet another instruction to proceed to a next step, the system may be configured to present a GUI via which to set the AC and PC positions. In an example embodiment, user interaction with any of the GUIs presented in sequence may be recorded and may accordingly impact the other GUIs presented at different points in the sequence, regardless of whether the other GUIs are displayed in response to a "Next" instruction or a "Back" instruction.

In an example embodiment, a progress bar may be provided that visually indicates a current location with respect to a sequence of steps to be performed, where the current location indicates the present step being performed. Each such step represented by the progress bar may refer to a particular user interface, where one or more, e.g., each, of such interfaces provide functionality for performing a number of substeps. Further, a first progress bar may be provided showing a location with respect to high-level steps, and a further progress bar may be provided showing a location with respect to low-level level steps within one of the high-level steps. For example, a first progress bar may show the steps of inputting patient information, e.g., by import of patient images and/or records, image/atlas registration, and programming. Within registration, a progress bar may show the steps of fusing MR and CT scans (or, in other embodiments, other images), selection of the MSP, selection of AC/PC, location of the lead tip(s), and location of the lead shaft(s).

With respect to import of images, the images may be imported from a system in which the images are associated with a patient record. The registration and/or programming system may include an import option for selecting an image from such an external system. In response to selection of the image from the external system, the system may automatically create a new patient file in the registration and/or programming system based on information of the patient record of the external system that is associated with the selected image. For example, any one or more of the patient name, age, gender, DOB, address, diagnosis, etc. may be imported and may automatically populate fields of an electronic record of the registration and/or programming system.

In an example embodiment of the present invention, the system may provide a patient listing, and for each listed patient, may indicate an active stage. The listing may be updated in response to import of information from an external system, as described above. With respect to the active stage, for example, if the image/atlas registration UI screens have not yet been completely traversed for setting the registration for a patient, the system may list that patient in a patient grouping under the heading "registration," while the system may list a patient for whom the registration has been completed in a patient grouping under the heading "programming." Moreover, the system may display for one or more, e.g., each, of the listed patients a status indicator showing a degree to which the stage has been completed. For example, for a patient for whom 75% of the registration steps have been performed, the system may display a circle, 75% of the perimeter of which is highlighted, or that includes a line or arrow extending from the interior of the circle towards a point on the perimeter of the circle corresponding to 75% of the circle, e.g., where the top-dead-center of the circle represents 0% and a clockwise rotation is assumed. Alternatively other markings relative to a circle or other geometric shape may indicate the completion percentage, e.g., the percentage of the shape that is filled may provide the indication.

Atlas Scaling

As noted above, image alignment and definition of the AC and PC locations may be used for registration between anatomical volumes of a patient and other defined volumes, e.g., of an anatomical atlas. Definition of the MSP may similarly define the line extending between the anterior and posterior extremities, the line extending between the superior and inferior extremities, and the line extending between the right and left extremities, which information may be useful for anisotropic scaling, described in detail below. The defined MSP may also be used for proper alignment of a three-dimensional volume such as that of another patient from a patient population or of an anatomical atlas with the patient image, according to which proper alignment, the non-patient volume may be registered to the patient's anatomy as reflected by the patient image.

For creating a patient-specific atlas, the system may provide a user interface via which a user may interact for initially lining up the patient MR to the atlas. This may be performed, for example, in the same manner as that described above with respect to aligning MR and CT images.

Alternatively, the system may additionally provide a user interface via which the user may additionally identify the mid-commissural point (MCP) in the patient image. The system may automatically align a patient image, e.g., an MR image, with the atlas subsequent to, and in accordance with, user input of the location of the MSP, AC/PC, and/or MCP in the patient image.

For example, the system may line up the AC/PC lines and/or MSP of the atlas and the patient MR, and may line up the MCP identified in the patient MR with the MCP of the atlas. Alternatively, the system may initially line up the atlas and the patient MR based on the AC/PC line and/or the MSP, and the user may then interact with a user interface provided by the system to shift one of the atlas and the patient MR relative to the other, to line up the point of the patient MR identified by the user as corresponding to the MCP with the MCP of the atlas.

The MCP is the mid-point between the AC and PC. Therefore, in an example embodiment of the present invention, subsequent to, for example, user-identification of the AC and PC, the system may automatically identify and record the MCP as the mid-point therebetween, user input not being required for such identification.

The distances between the respective AC/PC of each of the atlas and the patient MR can differ. The patient's MR image may therefore be required to be scaled relative to the atlas. In an example embodiment of the present invention, the system may scale the atlas (or other non-patient volume, e.g., from a patient population) automatically.

Figure 11:
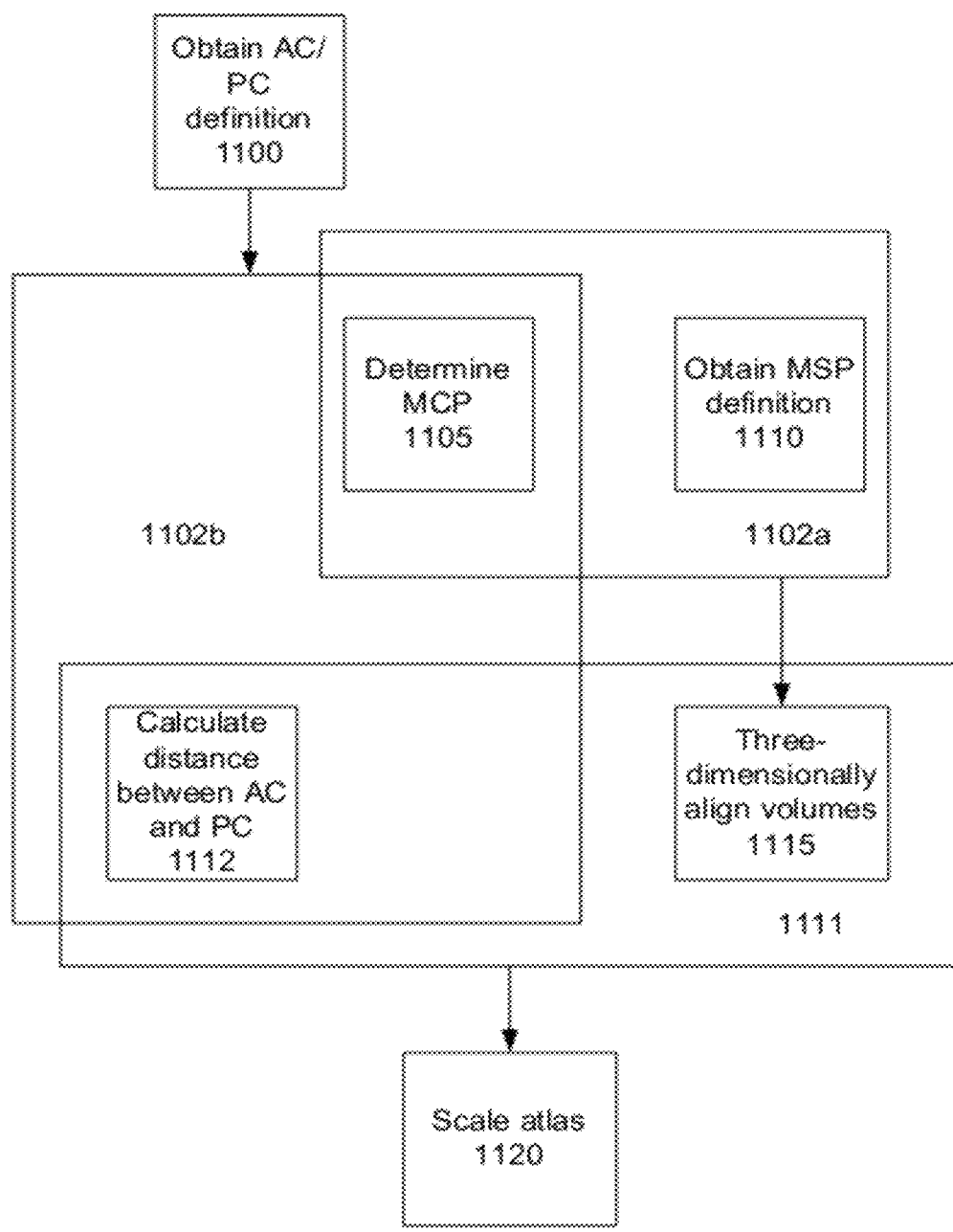
FIG. 11 is a flowchart that illustrates steps for scaling and aligning an atlas to conform to image data, according to an example embodiment of the present invention.

FIG. 11 is a flowchart that shows example steps the system may perform to automatically align and scale an atlas (or other non-patient) volume to the patient volumes represented in the patient image. At step 1100, the system may obtain the definition of the AC and PC, e.g., via user interaction with a user interface as described above. At step 1102*b*, the system may perform steps 1105 and 1112, e.g., in accordance with the AC/PC definitions obtained in step 1100. At step 1105, the system may determine the MCP as the mid-point between the AC and PC. Step 1105 may also be a part of a step 1102*a* on which basis the system may perform step 1115 described below. Step 1102*a* may also include step 1110. At step 1110, the system may obtain the definition of the MSP, e.g., via user interaction with a user interface as described above.

On the basis of step 1102*a*, including the determined MCP and obtained MSP, the system may perform step 1115. At step 1115, the system may three-dimensionally align the atlas (or other non-patient) and patient volumes.

Step 1115 may be part of step 1111. Step 1112, which is a part of step 1102*b*, may also be a part of step 1111. At step 1112, the system may calculate the distance between the AC and the PC based on the AC/PC definition obtained at step 1100. The calculation may be based on a known relationship, with which the system is programmed, between anatomical area and image pixels at various resolutions, and the distance in the image between the points to which the AC and PC were anchored.

Based on step 111, in which the volumes are aligned and the AC-PC distance is determined, the system may, at step 1120 scale the atlas (or other non-patient volumes) to approximately match the patient volumes.

The following are four example methods that may be used for performing the scaling.

In an example embodiment, the atlas is scaled linearly (by the same amount at all distances from the MCP) and isotropically (by the same amount in all directions).

In an example embodiment, the atlas is scaled linearly and anisotropically (by different amounts in different directions). In this regard, the inventors have discovered that an anisotropic scaling of the atlas would usually result in a better fit to patient volumes than an isotropic scaling.

In an example embodiment, the atlas is scaled non-linearly (by different amounts at different distances from the MCP) and isotropically. In this regard, the inventors have discovered that a non-linear scaling of the atlas would usually result in a better fit to patient volumes than a linear scaling.

In an example embodiment, the atlas is scaled non-linearly and anisotropically.

Referring to the linear and isotropic scaling, in an example embodiment, the atlas may be stretched or contracted equally in all directions including right, left, the anterior direction, the posterior direction, the inferior direction, and the superior direction, with the MCP remaining in place, until the distance between the AC and PC of the atlas equals the distance between the AC and PC of the MR image.

Figure 12:
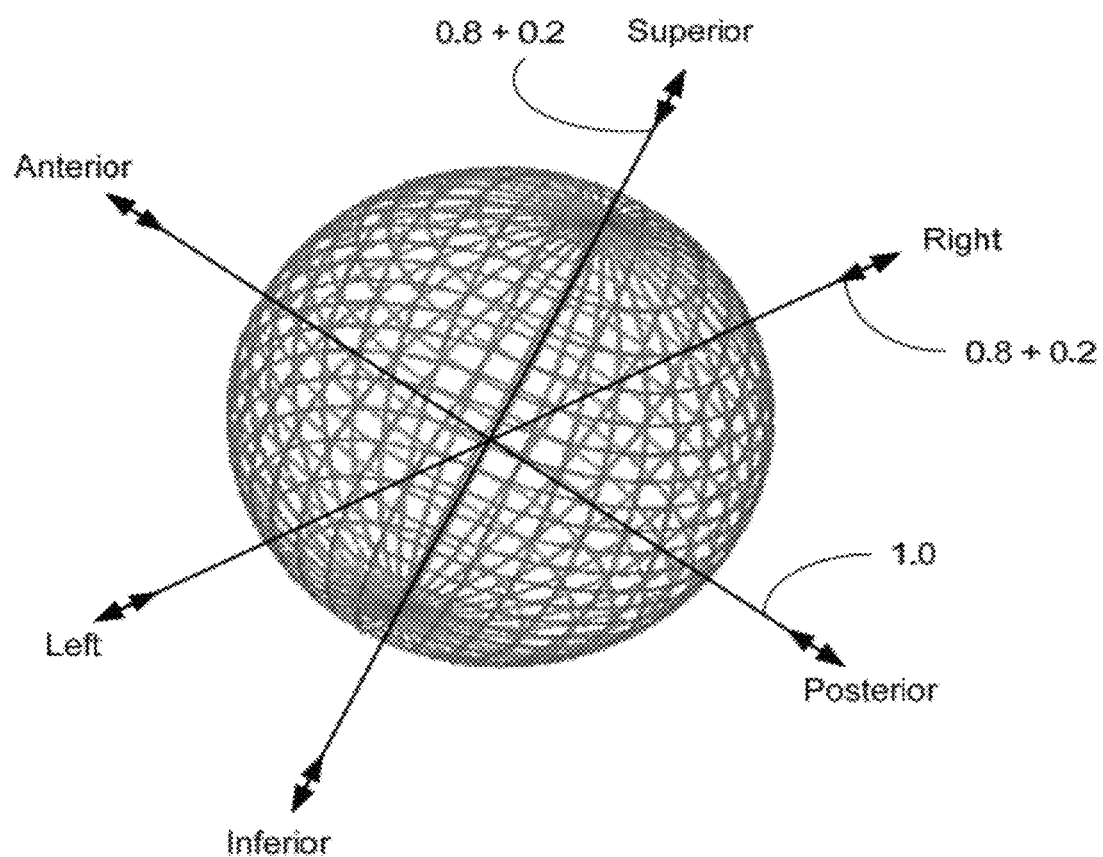
FIG. 12 shows relative scaling amounts for an anisotropic atlas scaling, according to an example embodiment of the present invention.

However, it has been determined that, while the above method may provide a rough atlas of the patient brain, it is often advantageous to scale the atlas anisotropically. For example, it is often advantageous to scale the atlas in the anterior and posterior directions, i.e., in a direction approximately parallel to the line connecting the AC and PC, to a greater extent than in other directions. Therefore, in an example embodiment, the scaling in the superior and inferior directions and to the left and the right may be, for example, to approximately 0.8 the amount by which the atlas is scaled in the anterior and posterior directions. For example, as shown in FIG. 12, the anisotropic scaling may be by the following factors:

$$a = \frac{AP_{MR}}{AP_A};$$

$LR_{MR}=(0.8*a+0.2)*LR_A$; and $DV_{MR}=(0.8*a+0.2)*DV_A$, where $AP_X$ is the distance in the anterior-posterior directions, $LR_X$ is the distance in the left-right directions, $DV_X$ is the distance in the superior-inferior directions, $X_{MR}$ is the distance in the patient's MR space, and $X_A$ is the distance in the original atlas space. The 0.8 factor was determined by examining the respective ratios of the length of the brain in each of anterior/posterior, left/right, and superior/inferior directions to the distance between the AC and PC in a number of patients, and then examining the ratio of the left/right ratio to the anterior/posterior ratio and the ratio of the superior/inferior ratio to the anterior/posterior ratio. In nine studied patients, it was found that the ratio of the anterior/posterior distance to the AC-PC distance was an average±standard deviation of 6.07±0.66; the ratio of the left/right distance to the AC-PC distance was an average±standard deviation of 4.85±0.52; and the ratio of the superior/inferior distance to the AC-PC distance was an average±standard deviation of 4.84±0.42. Therefore, the ratio of the left/right ratio to the anterior/posterior ratio was 4.85/6.07=~0.8, and the ratio of the superior/inferior ratio to the anterior/posterior ratio was 4.84/6.07=~0.8.

The 0.2 offset may be applied because of the possibility that the distance between the AC and PC in the atlas and in the patient MR are equal or substantially equal, such that no scaling is required in the anterior/posterior direction, in which case the 0.2 offset would provide that no scaling is performed in the other directions as well.

In an example embodiment of the present invention, the system may be updated over time with information regarding ratios of the lengths of the brain in the different directions for different patients, and the system may recalculate the factor by which to perform the anisotropically scaling in accordance with such updated information.

As noted above, it has also been determined that it may be beneficial to non-linearly scale the atlas. For example, the system may scale the atlas by a lesser degree at greater distances from the MCP than at smaller distances (or vice versa). Further, whether to linearly or non-linearly scale the atlas may depend on the direction. For example, the atlas may be linearly scaled in the anterior and posterior direction and non-linearly scaled in the other directions, where the scale amount is inversely proportionate to the distance from the MCP, i.e., the greater the distance, the less the scale factor.

In an example embodiment, the system may be programmed with a predefined function to scale the atlas as a function of the difference between the AC-PC distance of the atlas and that of the patient and as a function of distance between the coordinate of the atlas being scaled and the MCP. In an alternative example embodiment a different anatomical landmark other than the MCP may be selected as that to which a distance is measured and used for determining the degree of scaling.

In an example, the system initially scales the atlas linearly, e.g., as a function of a difference between the AC-PC distance of the atlas and that of the patient, and provides a user interface by which the user may provide input for modifying the atlas with a non-linear scaling, for example, using a user interface as described in, e.g., the '330, '312, '340, '343, and '314 applications concerning FIGS. 9 and 10 of the '330, '312, '340, '343, and '314 applications.

While the above has been described with respect to the AC, PC, MSP, and MCP, it is noted that the initial alignment of the patient MR and the atlas may be performed using other landmarks, and while the centering, stationary registered point about which the scaling is performed has been described above as the MCP, it is noted that other landmarks may be used as the stationary registered point about which the scaling is performed. For example, other landmarks may be used where the most relevant anatomical regions are of different portions of the brain in which the AC, PC, MCP, and/or MSP are not the most relevant part, or where the focus of the stimulation is an anatomical region other than the brain.

In an example embodiment, the system may be preconfigured with settings for automatically scaling the atlas in the described ways and/or the described amounts. In an example embodiment, the system may provide a user interface for inputting scaling values on a per direction basis, and/or for inputting a scaling factor as a function of distance, e.g., on a per direction basis.

While the above methods for scaling of the atlas have been described with respect to an MR image, the methods may be similarly applied to other imaging modalities. For example, after a CT is registered to an MR and the AC and PC registered in the CT, the atlas may be lined up with the CT and the scaling of the atlas may be to the CT image.

Automated Atlas Registration

Rigid, Affine, and B-Spline Registration with or without Skull Stripping

In an example embodiment of the present invention, a patient atlas may be automatically generated without use of identified points, e.g., AC, PC, MCP, MSP, within the patient image. According to this method, steps for identification by the user of the MSP, AC, and PC, as described above, may be omitted.

The system may store a plurality of MRs of a patient population and corresponding atlases generated for those MRs. In an example embodiment, the system may further store an atlas that is an average of the individual atlases corresponding to the MRs of the patient population. In an example embodiment, the system may further store, for each of a plurality of subsets of the patient population MRs, a respective average atlas. The subsets may be formed by grouping MRs by one or more metrics selected from a group of metrics including patient condition, such as disease indications and/or injuries; patient age; patient sex; patient height; patient weight; overall brain size; target VOA; and/or MR scan type (e.g., T1 or T2).

The system may select one of the stored atlases for automatic registration to the patient MR. The selection may be based on comparison of one or more metrics selected from a group of metrics including patient condition, such as disease indications and/or injuries; patient age; patient sex; patient height; patient weight; overall brain size; target VOA; and/or MR scan type (e.g., T1 or T2).

According to an embodiment in which target volumes are used for selection of patient population MR(s), if there are multiple target volumes, the system may use an average or a weighted average of the volumes. Which target volumes to use as the basis for the selection and/or the weights of the various volumes may be manually selected or may be automatically selected, e.g., based on importance of the respective target volumes for treating the patient's disease state.

The selection may alternatively or additionally be based on MER data. For example, the atlas corresponding to the stored MR image associated with MER data most closely matching that of the patient may be selected. The MER data may be a factor considered in addition to a result of a mutual information algorithm which determines a similarity between images. For example a function may be used to determine similarity which weights different factors, such as MER data and mutual information.

In an example embodiment, the system may select a subset of the patient population based on factors delineated above, and then select the average atlas of that subset.

In an example embodiment, the system may always select the average atlas of all of the patient population.

In an alternative example embodiment, an average atlas, e.g., that of all of the patient population or that of a particular subset of the patient population may be selected only if no single stored MR image of the patient population is determined to be sufficiently similar to that of the patient's MR image and/or if the MER data and/or the other used factors are not sufficiently similar.

The system may then warp the selected patient population MR, to which an atlas has been registered, to the patient MR image to obtain a patient-specific atlas, using one or more image registration processes. A mutual information algorithm may then be used to determine how well the atlas has been modified by the registration processes.

In an example embodiment, the system may register the selected atlas to the patient MR image using a rigid registration. The rigid registration includes a rotation and/or a translation of the atlas, but does not include scaling.

In an alternative example embodiment, the system may perform a transformation method which the inventors have discovered produces a more precise atlas registration. The method includes performing a rigid registration followed by an affine registration of the patient population MR. The affine registration may include a modification of the type x→Ax+b, where Ax is a linear transformation, and +b refers to a translation, and/or may include a translation, a rotation, scaling, and/or shear tranforms. The affine registration may include a non-linear and/or anisotropic modification of the patient population MR, e.g., where the non-linearity and anisotropy is as described above. The rigid registration may be initially performed to provide a better starting point for performance of the more complex affine registration, providing for a faster and more accurate registration than performance of just the affine registration. The inventors have discovered that performance of the affine registration following the rigid registration usually provides a more accurate patient atlas than where only the rigid registration is performed.

In an alternative example embodiment, the system may perform a transformation method which the inventors have discovered produces an even more precise atlas registration. The method includes performing a rigid registration, followed by an affine registration, as described above, followed by a B-spline registration. Alternatively, the B-spline registration may be performed prior to the affine registration. The B-spline registration may include a non-linear and/or anisotropic modification of the patient population MR, e.g., where the non-linearity and anisotropy is as described above. The affine registration may act on the patient population image and the current patient image as a whole, whereas the B-spline registration may act on smaller sub-volumes of the images. The rigid registration may be initially performed to provide a better starting point for performance of the more complex affine and B-spline registrations, providing for a faster and more accurate registration than performance of just the affine and/or B-spline registration. Additionally, there is a chance that a B-spline registration algorithm performed directly on the original patient population image would fail because a B-spline registration algorithm might not be able to resolve images that are too dissimilar.

In an alternative example embodiment, the system may perform a variant of the above-described registrations which the inventors have discovered produces an even more precise atlas registration. The method includes initially removing portions of the image corresponding to the patient's skull, and then performing one of the above-described registration methods, i.e., rigid, rigid+affine, or rigid+affine+B-spline. The skull may be irrelevant to the registration process. Removal of the skull data would allow the algorithms to base the transformation on a greater percentage of relevant information.

While it is advantageous to perform a combination of skull stripping, rigid registration, affine registration, and B-spline registration for obtaining a precise registration, in an example embodiment it may be advantageous to omit one, some, or all of the skull stripping, affine registration, and B-spline registration steps, to reduce processing load, e.g., depending on processing capacity of the device being used.

Figures 13, 14:
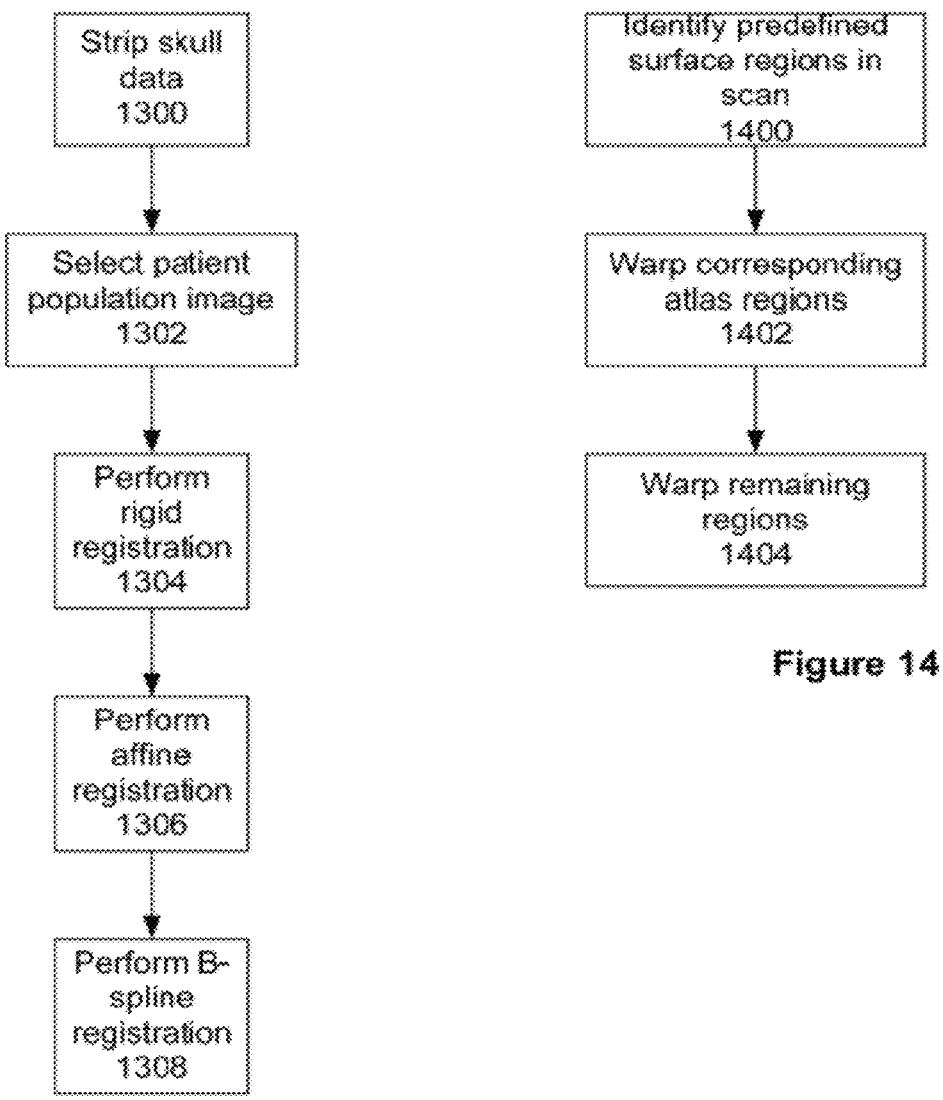
FIG. 13 is a flowchart that illustrates steps for registering a patient population image atlas to a current patient image, according to an example embodiment of the present invention.
FIG. 14 is a flowchart that illustrates a method for obtaining a patient-specific atlas, according to an example embodiment of the present invention.

Accordingly, referring to FIG. 13, in an example embodiment of the present invention, the system may, at step 1300, remove image data from the patient's MR image determined to represent the skull. At step 1302, which may be performed, for example, subsequent to step 1300 in an example embodiment, the system may select a patient population image from a repository of patient population images to which respective atlases have been registered. At step 1304, the system may perform a rigid registration to warp the selected patient population image, e.g., MR, to fit the skull-stripped patient image. At step 1306, the system may subsequently perform an affine registration of the thus far warped patient population image to further warp the image to better fit the skull-stripped patient MR. At step 1308, the system may subsequently perform B-spline registration of the thus far warped image to further warp the image to better fit the skull-stripped patient MR.

In an alternative example embodiment of the present invention, instead of initially selecting just one patient population image to which to apply the one or more described registration and/or skull stripping procedures, the system may initially select more than one, e.g., all or a subset including less than all, of the patient population images. According to an embodiment where a subset including less than all of the patient population images is selected, the subset may be selected from the plurality based on the above-described image selection factors. The system may apply the registration and/or skull stripping features described above to all of the subset of the selected images.

The system may subsequently average the warped versions of the images to obtain the patient-specific atlas.

Alternatively, the system may determine a weighted average of the warped versions of the selected patient population images. For determining the weights, the system may determine the similarity between the respective patient population images to which atlases correspond and the patient image, and, based on the determination of the similarity, a degree to which the patient population image should contribute to the final atlas registration. For example, for this purpose, a mutual information algorithm may be performed to determine the similarity between the images.

In an example embodiment, the image comparison algorithm may be performed completely or primarily in the regions corresponding to the target regions. That is, even where the registered images are not similar overall, they may be similar in the relevant regions, and vice versa. Moreover, various target regions may be ranked, with higher weightings given to the higher ranked target regions. An overall similarity score may be calculated based on the similarities of the various target regions and/or the remaining regions, as modified by the weightings. The overall score may be used to determine the degree to which the corresponding patient population image should contribute to the final patient atlas. In an example embodiment, the overall image similarity of the image as a whole may be additionally be factored into the equation for generating the similarity score.

Feature Extraction

In an alternative example embodiment, the selected atlas, e.g., selected based on the factors described above, is registered to the MR image as follows. First, the system finds certain predefined surfaces in the MR image, e.g., those of the ventricles and/or Thalamus. For example, such surfaces may be found by the system by performing a pattern matching algorithm to find matches to corresponding predefined structures of the atlas. The system then automatically warps the corresponding predefined surfaces in the atlas to the identified surfaces of the MR image, e.g., such that the warped three-dimensional atlas structures at least approximate the identified surface regions in the MR. The system may then warp remaining portions of the atlas incidental to the warping of the regions corresponding to the predefined surfaces.

For example, the system may use a 3-D registration algorithm to minimize differences between 3-D data of the patient scan, and 3-D data of the atlas. For example, one such registration may include a non-rigid inter-subject brain surface registration using conformal structure and spherical thin-plate splines. However, other suitably appropriate registrations may be performed instead. Remaining portions may then be incidentally modified automatically, e.g., according to the incidental warping method described in the '330, '312, '340, '343, and '314 applications concerning FIGS. 9 and 10 of the '330, '312, '340, '343, and '314 applications. Thus, referring to FIG. 14, according to an example embodiment of the present invention, the system may, at step 1400, find predefined three-dimensional surface regions in a patient scan. At step 1402, the system may warp corresponding surface regions of an atlas to match the identified surface regions of the patient scan. At step 1404, the system may warp portions of remaining regions of the atlas incidental to the warping of the predefined surface regions.

Alternatively, the automatic registration of the surfaces may determine an overall scaling/translation/rotation matrix to apply to the atlas as a whole. In an example embodiment, for determining the matrix to apply based on the automatic registration of the surfaces, different ones of the registered surfaces may be weighted differently in the calculation of the matrix. For example, certain ones of the registered surfaces may be considered to be of greater importance than others in the determination of the atlas registration and may be set to have applied thereto a greater weighting in the determination of the matrix. In an example embodiment, the weightings may vary depending on the patient, e.g., depending on patient condition and/or the regions targeted for stimulation for the patient. (Different regions may similarly be weighted differently for determining a matrix for modifying one image to be registered to another image.)

In an alternative example embodiment, the system may identify the predefined surfaces and visually demarcate the surfaces in the patient image, e.g., the MR image. A user may use a user interface to line up the atlas with the MR image in a position where one of the atlas and MR image overlies the other of the atlas and MR image. The system may provide atlas modification controls via which a user may shift the surface regions of the atlas to at least approximately correspond to the positions of the surfaces identified in the MR image, for example, according to the methods described in the '330, '312, '340, '343, and '314 applications concerning FIGS. 9 and 10 of the '330, '312, '340, '343, and '314 applications. Remaining portions may be incidentally modified, e.g., according to the methods described in the '330, '312, '340, '343, and '314 applications concerning FIGS. 9 and 10 of the '330, '312, '340, '343, and '314 applications. Alternatively, the registration of the surfaces as defined by the user's input, may determine an overall or local scaling/translation/rotation matrix, which the system may automatically apply to the atlas as a whole.

In an example embodiment of the present invention, the system may automatically determine how the atlas should be registered to the image (or how two images should be registered to each other) according to methods described herein, or according to any suitably appropriate method. When the user performs the manual registration, the system may output an indication of how well the items have been registered by comparison to the automatically determined registration. The user can ignore the indication or may further modify the registration based on the indication. In response to such further modification, the system may update the output indication of the degree of accuracy of the registration. In an example embodiment, multiple such indications may be output, each for a respective anatomically significant region. Those regions considered to be significant for such output may depend on the patient, e.g., based on the patient condition and/or those regions of the patient targeted for stimulation. In an example embodiment, the user may input the regions for which such output should be provided. In an example embodiment, different regions may be displayed in different views, and in one or more, e.g., each, of the views, the indications relevant to the displayed regions may be output.

Auto-Determine a Lead Type and Hemisphere Using a Post-Op Image

The system analyzes a CT, MR, or an image of another imaging modality, to determine where a leadwire is located, including whether there is only one leadwire or two or more. If there is only one leadwire, the system determines and records whether the leadwire is in the left hemisphere or the right hemisphere. The system may identify the number and type of leadwires implanted by searching for matches to particular patterns in the post-op image. This may be useful for determining the correct number of programming interfaces to provide to the user via a user interface, e.g., one programming interface per lead, and the correct stimulation field models to apply when performing programming. The leadwire type and location may also be useful from a user perspective, when the user does not know how many leadwires are implanted or where the leadwires are located. In an example embodiment, this information may be output to the user as a confirmation step at the conclusion of image analysis.

According to an example embodiment, leadwire type and/or location may be determined by stepping through a series of CT image slices and tracking changes in image features generated by the leadwires. The determination can be made, for example, by removing all of the CT data but for the saturated data, which would leave only or substantially only an outline of the skull and a representation of the leadwire. The outline of the skull can be ignored by the system, e.g., since it does not match an expected approximate shape for the leadwires, and/or recorded by the system as the skull.

FIG. 15 shows a series of images 1500A to 1500D representing CT slices taken in the axial view. Each slice may include a brain outline 1550 and one or more leadwires 1500. On an actual CT, brain structures generally correspond to dark areas inside the brain outline 1550, whereas the leadwires 1500 tend to show as white dots. This is because of the different densities of leadwires compared to the surrounding brain tissue, i.e., the leadwires are much more dense than the brain tissue. Additionally, because the skull is also more dense than the brain, it will be appreciated that ignoring the skull outline may facilitate distinguishing of the leadwires.

As the slices progress from 1500A to 1500D, the leadwires 1500 may vary in cross section, e.g., decreasing in diameter towards the tip. It is noted that FIG. 15 is not to scale, but is intended to show generally that the size of the representations of a leadwire can vary between slices. Eventually, the dots corresponding to the leadwires 1500 each may be reduced in size to form a point at a slice corresponding to a location near the very tip of the leadwire, and then disappear entirely from subsequent axial image slices. Thus, the location of tips may be determined as corresponding to the slice(s) in which each respective leadwire forms a point. Additionally, the system may determine a leadwire trajectory based on how the leadwire cross sections move from slice-to-slice. For example, a directional vector may be calculated that connects the center of each dot to represent the trajectory.

Although the leadwires were described as being represented as dots in the axial view, it will be understood that the sagittal and coronal views may have more than a dot representative of the leadwire in those slices through which the leadwire passes. For example, FIG. 16 shows a series of images 1600A to 1600D representing CT slices in the sagittal view, where the leadwire cross sections may be substantially cylindrical. Depending on the trajectory and/or shape of the leadwire, different portions of the leadwire are shown in each sagittal slice. Thus, slice 1600C shows only a tip-most portion of a leadwire 1610, whereas slice 1600B shows the entire length of the leadwire 1610. The leadwires can be located in relation to the skull, which may be separately detected as noted above, and/or may be located relative to other anatomical regions of the brain as determined by registration of the CT with an MR to which an atlas is registered.

The system may also automatically determine the type of the leadwire. For example, different leadwires may have different lengths. The system may include a database of leadwire types in association with their respective lengths. The system may calculate the length of a leadwire based on the number of axial slices in which the leadwire appears, and/or based on its length in a coronal and/or sagittal slice. The system may look up the database to determine the type by finding the leadwire-type having the associated length closest to the detected length of the leadwire. Alternatively, the database may associate leadwire types based on varying diameters and find the type having the closest matching diameter to a stored leadtype.

In an alternative example embodiment, the system may determine the type of a leadwire based on a pattern matching algorithm. For example, the system may store in a database leadwire types in association with respective distinct patterns. Each leadwire type may have a different cross-sectional shape in one or more of the three views. For example, an axial cross-section of a leadwire having a single non-directional contact is easily distinguished from an axial cross-section of a leadwire having three directional contacts. The system may match the patterns of the leadwires detected in the CTs to the stored patterns and identify the leadwire as that associated in the database with the closest matching pattern. It is noted that the CT detected leadwire patterns may be different than an outline of the actual leadwires. That is, the CT images may include image artifacts such that a direct comparison to the actual outline may not be possible. Expected CT detected patterns may be generated, for example, by averaging together corresponding slices of CT images containing known leadwire types. Accordingly, the system may store in the database the expected CT detected patterns rather than the outlines. Alternatively, the outlines may be stored and the pattern-matching algorithms may match the detected pattern to the expected detected patterns for the stored outlines. That is, the effects of artifacting may be known, so that the system may take potential artifacting into consideration when comparing the detected patterns.

In an alternative example embodiment, markers which geometrically differ between leadwire types may be placed on the leadwires. The system may detect the geometric marker and match it to one stored in a database in association with a respective leadwire type, in order to determine the leadwire type. The detection of the geometric marker and the matching may be performed using a three-dimensional volume. For example, the system may store in a database a plurality of three-dimensional representations of different types of leadwires. The system may also generate a three-dimensional representation of the imaged leadwire, e.g., for at least a portion of the leadwire that includes the geometric marker. The stored representations may then be compared to the generated representation to determine a degree of fit between the representations.

In an example embodiment, the stored representation is overlaid onto the generated representation and the degree of fit is determined by calculating a degree of overlap between the representations. For example, the system may conclude that the imaged leadwire is of the same type as one of the stored leadwire representations where a threshold amount of the representation of each is overlapped by the other.

In an alternative example embodiment, a non-electrode marker is positioned on different leadwires at different distances to an adjacent electrode. The system may detect the distance of the marker from its nearest electrode. The system may match the detected distance to recorded distances in a database, each associated with a respective leadwire type.

Automatically Locate Leadwire Based on Registered CT Image and Trajectory and Depth Information In an example embodiment of the present invention, the system may automatically identify the location of a leadwire based on (1) a CT image taken prior to implantation of the leadwire, which CT image is registered to an MR image in which anatomical structures may be recognized, and (2) information, e.g., input by a clinician, indicating (a) a ring and arc angle of a headframe used for insertion of the leadwire, (b) the depth of the leadwire insertion, and/or (c) the leadwire that is used. Information such as (a), (b) and (c) is typically input during pre-surgical planning and stored, for example as handwritten notes or stored into a clinician-accessible database or a memory device such as a CD-ROM, a DVD, a flash memory, etc. The information may also be updated during surgery based on changes to a surgical plan, e.g., a new leadwire type, entry point or trajectory. After surgery, the information may be input into the system using e-mail (within a body of the e-mail or as an attachment), wireless transmission, the Internet or, in the case of a portable computer-readable storage medium, physically transferred via a media reader such as a DVD drive. The system may determine the length of the leadwire based on the information concerning which leadwire was used. Alternatively, the system may make the determination without the information regarding the leadwire type, if the insertion depth information is a measure of the depth at which the bottom tip of the leadwire penetrates the anatomy.

Figure 17:
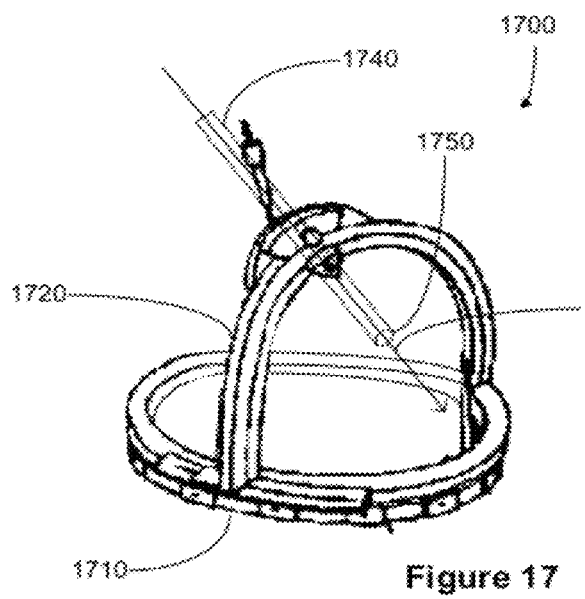
FIG. 17 shows a headframe including an arc and ring that define a trajectory of a leadwire, according to an example embodiment of the present invention.

For example, in a surgical planning stage, a leadwire trajectory may be selected. The trajectory may be for a leadwire to be implanted in a brain, and may be relative to a headframe, e.g., a headframe 1700, as shown in FIG. 17. The headframe 1700 may include a ring 1710 extending within a plane approximately parallel to an axial brain slice. The headframe may further include an arc 1720 attached to the ring 1710. The arc 1720 may be rotated about the ring 1710 to change the ring angle, and the insertion guide may be shifted along the arc 1720 to change the arc angle. The combination of the ring and arc angle may define a planned trajectory 1730. Such information may be used by the system as the trajectory information for determining the location of the leadwire.

In an example embodiment, for locating the headframe relative to the patient's head, a CT image, taken after screws have been inserted into the patient's head (e.g., at specific reference points on the head) via which the headframe is attachable to the patient's head, may be registered to the MR image. Based on the location of the screws, the position of the headframe, and thus the leadwire whose trajectory is defined by angles of the headframe, relative to the MR image and its included brain structures is known. To illustrate, in FIG. 17 the system may calculate a length of a leadwire 1740 and a location of its tip 1750, based on an insertion depth and the trajectory 1730 input by the clinician. The system may then calculate a set of coordinates for the leadwire 1740 relative to the registered CT image, e.g., CT image space coordinates corresponding to the leadwire tip and a position along the leadwire shaft.

In an example embodiment of the present invention, arc and ring angle, and target location for end-point of leadwire may be user input directly into an image registration system and/or module and/or directly into a stimulation programming system and/or module. In an alternative example embodiment, as noted above, arc and ring angle, and target location for end-point of leadwire may be input into a surgical implantation module, used for planning and conducting surgery for implanting the leadwire, and may imported into the image registration and/or programming system and/or module. Alternatively, based on such information obtained in the surgical implantation module, the system may record coordinates of the leadwire. Such coordinate information may be imported by, for example, the stimulation programming module, and used by the model for generating a model of the leadwire positioned relative to anatomical structures of the brain. In this manner, the leadwire coordinates need not be extrapolated based on information subsequently input into the system after surgery has occurred. Instead, the information is made available to the system from an early point in time, e.g., during planning. The CT image may be registered to an MR image by the surgical implantation module, or may be imported by the programming (and/or registration) module for registration of the CT image with an MR image, e.g., using methods described above. (An atlas may also be registered to the MR image, e.g., using methods described above, such that the leadwire model may be positioned relative to atlas features.)

Directional Auto Lead-Location

In an example embodiment, the system may automatically determine a rotational position of a leadwire by analysis of shapes formed in CT images of the patient at an anatomical region at which the leadwire is positioned. The use of geometric markers as described above in connection with the auto-determination of leadwire type, may also facilitate determination of leadwire directionality. For example, a geometric marker may generate a distinct CT pattern so that the pattern indicates a single direction, e.g., a point along a circumference of a leadwire cross section on the CT images. Example geometric markers that may be used in conjunction with the system of the present invention are described in the '330 application, in connection with FIGS. 24A-B, 25A-B and 26. In FIGS. 24A-B, the leadwire includes a pair of windows that can be shifted relative to each other (e.g., rotated or offset). In FIGS. 25A-B and 26, triangular marker bands are used to provide directional references for determining the orientation of leadwire electrodes. Other example markers include a strip extending longitudinally down one side of the leadwire or a such a strip with circumferential band extending around the leadwire, for example at or near each end of the strip. Such circumferential bands may be provided for proper alignment of the marker with the leadwire, for ease of manufacturing.

In an example embodiment, the rotational location may be automatically determined by comparing multiple shapes formed in different CT image slices. The compared shapes may be formed in axial CT slices. However, slices from any of the viewing axes may be used in a similar fashion.

Figure 18:
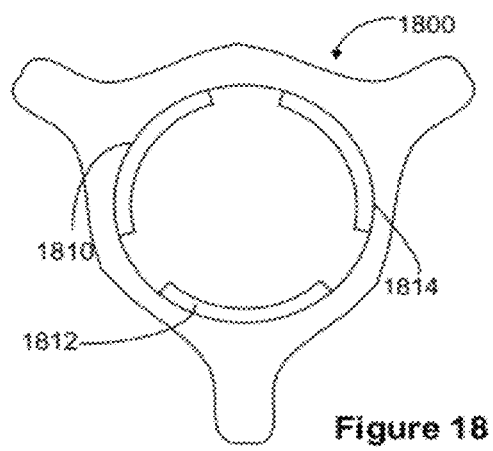
FIG. 18 shows a representative CT slice that includes features formed by a plurality of directional electrodes in a leadwire, according to an example embodiment of the present invention.
Figure 19:
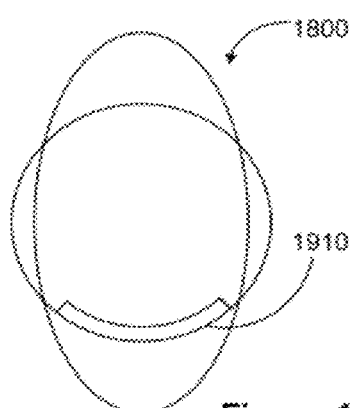
FIG. 19 shows a representative CT slice that includes features formed by a non-electrode in the leadwire of FIG. 18, according to an example embodiment of the present invention.
Figure 21:
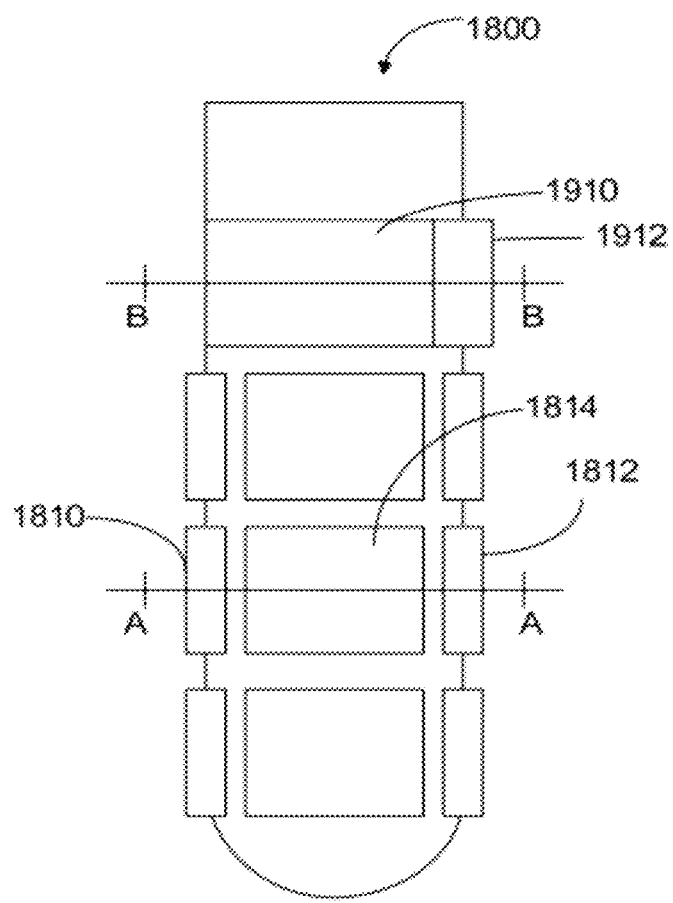
FIG. 21 shows a profile view of a leadwire, according to an example embodiment of the present invention.

When comparing multiple shapes, one of the shapes may be a geometric marker, e.g., a non-electrode element, and another of the shapes may be an electrode element. For example, FIG. 18 shows an axial CT slice of a leadwire 1800 in which three electrodes 1810/1812/1814 are arranged about the perimeter of the leadwire, e.g., at equal distances from each other. FIG. 19 shows a different axial CT slice of the same leadwire 1800. The cross section of FIG. 19 may, for example, correspond to a portion further from the tip than the portion to which the cross section of FIG. 18 corresponds. A non-electrode element 1910 may be arranged at a different level of the leadwire as shown below. The non-electrode element may be made of the same material as the electrodes. For example, it may be an unconnected, and non-functional, electrode, also known as a dummy electrode. FIG. 21 shows an example profile view of the leadwire 1800 along a longitudinal axis. The CT slice of FIG. 18 may be taken along line A-A and the CT slice of FIG. 19 may be taken along line B-B.

Figure 20:
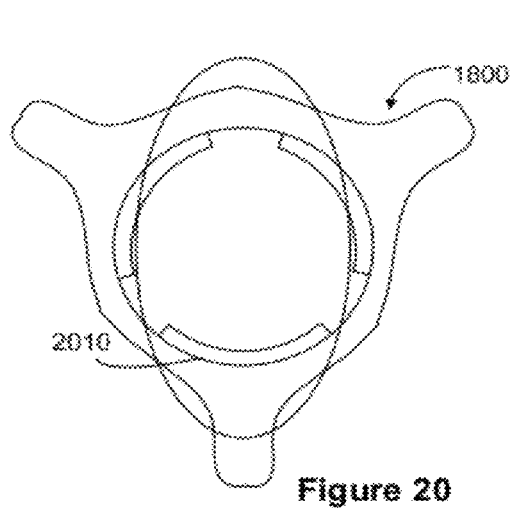
FIG. 20 shows a composite image formed by combining the representative slices of FIGS. 18 and 19, according to an example embodiment of the present invention.

As shown in FIG. 21, the non-electrode element 1910 includes a protrusion 1912 that rotationally coincides with the electrode element 1812. The protrusion 1912 serves as a distinguishing feature on the non-electrode element 1910, as opposed to a remaining portion of the non-electrode element 1910, which is substantially flush with a body of the leadwire. The non-electrode element 1910 may be rotationally positioned about a center longitudinal axis of the leadwire such that it coincides with the rotational position of one of the 3 electrodes 1810/1812/1814. The artifact in the axial CT image slice caused by the 3 electrodes 1810/1812/1814 may have a triangle-like shape, with three noticeable primary vertices, each corresponding approximately to a center of a respective electrode. The artifact in the axial CT image slice caused by the non-electrode element 1910 may have an oval-like shape including two noticeable vertices (or a rectangular-like shape with two short sides) that are opposite each other. One of the vertices corresponds to the protrusion 1912, while the other extends in an opposite direction. Due to the rotational orientation of the non-electrode element 1910 with respect to the center axis and relative to the rotational orientation of the electrodes 1810/1812/1814 with respect to the center axis, when the axial slice including representations of the 3 electrodes 1810/1812/1814 and the axial slice including the representation of the non-electrode element 1910 are lined up, one of the two primary vertices of the slice of the non-electrode element 1910 will correspond with one of the vertices of the triangle-like shape (e.g., the vertex corresponding to the electrode 1812), while the other of the two primary vertices will not correspond to any vertex of the triangle-like shape, as shown in FIG. 20.

The system may therefore identify the electrode with which the non-electrode lines up by identifying the vertex overlap. Based on the identification of the electrodes, the system may properly set and/or control which electrodes to turn on and/or the respective amplitudes to be applied to the respective electrodes for a stimulation. For example, the system may determine which electrodes face which respective anatomical regions, and may accordingly operate the correct electrodes in the correct manner for producing the intended VOA. Similarly, the system may correctly rotationally model the leadwire relative to the patient anatomy, so that a clinician may correctly input stimulation parameters associated with particular ones of the electrodes according to the positions of the electrodes relative to various anatomical regions.

In an alternative example embodiment, instead of comparing the two artifacts to see where primary vertices of each line up, the system may combine the two artifacts into a single artifact by overlapping the two artifacts. The system may then pattern match the combined artifact to a stored pattern. Rotational positions of the electrodes may be identified relative to the stored pattern. By aligning the combined CT artifact to the stored pattern, the system may apply the rotational position identifications of the pattern to the aligned combined CT artifact, thereby identifying the rotational locations of each of the electrodes.

In an alternative example embodiment, instead of a non-electrode element having a structure similar to that of the electrodes, a strip may extend longitudinally down one side of the leadwire, which causes a CT artifact having a single point. The electrodes on either side of the strip, and thus also any remaining electrodes may be identified.

In an example embodiment of the present invention, the system may provide a user interface via which to obtain user-placed markers and/or user-input location information the system may then use for determining the position and orientation of the leadwire. A user may manually select a location of the tip of the leadwire, a point on its shaft, and a point at which a directional marker is located. For example, these landmarks may be recognizable by a user in displayed images. The user may place a marker at, or otherwise select, a region of an axial image slice corresponding to a center of the lead tip, and the user may place a marker at, or otherwise select, a region of an axial image slice corresponding to a center of one part of the shaft. The user may place a marker at, or otherwise select, a region of a coronal or sagittal image slice corresponding to a region at which the marker on the leadwire is located, thereby indicating the orientation of the leadwire. The system may then display a model of the leadwire according to the user-placed markers, within a representation of an anatomical volume of the patient.

Import Patient Data from an External Source

Figure 22:
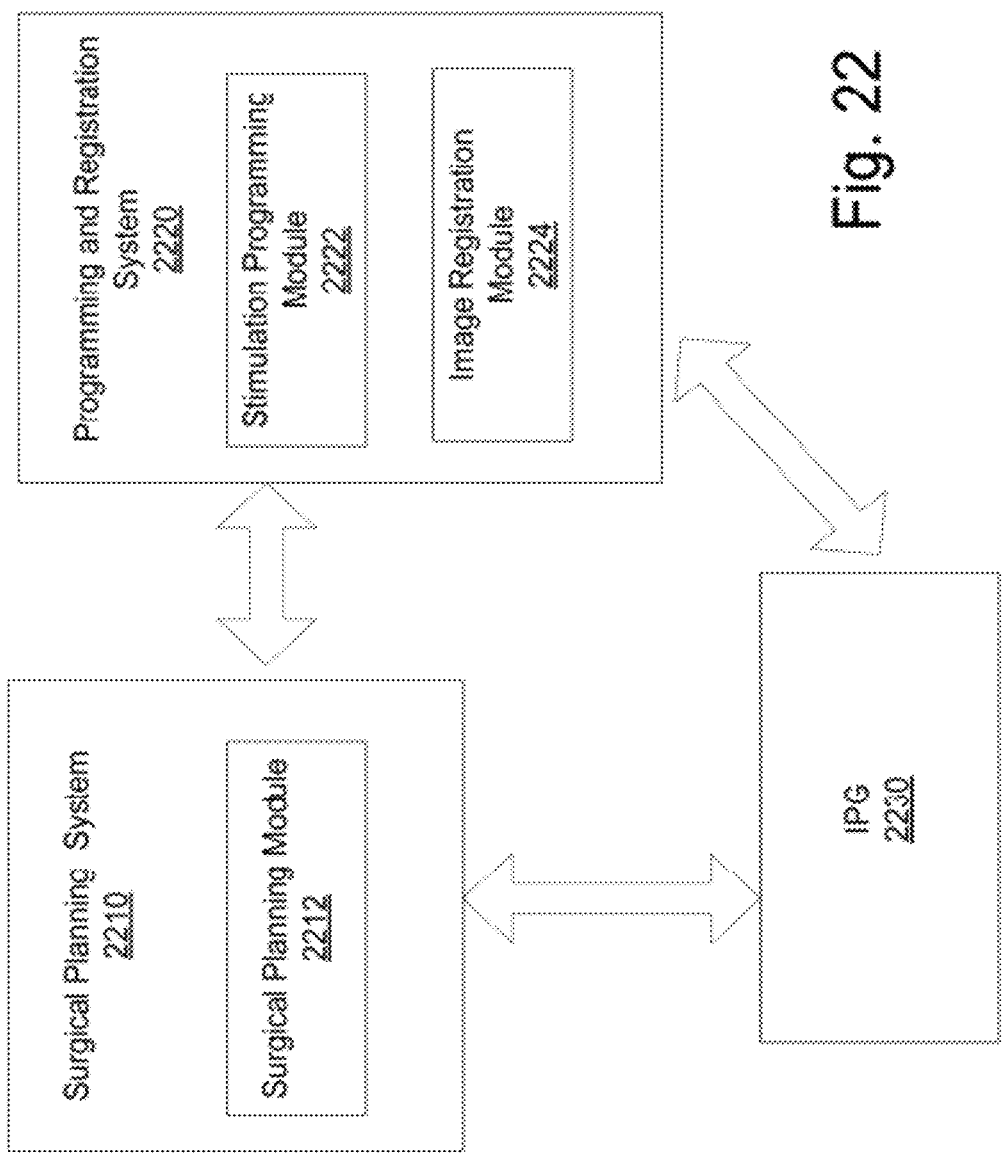
FIG. 22 shows a block diagram of a system, according to an example embodiment of the present invention.

Patient data such as brain images (pre-implantation and/or post-implantation), clinical notes, leadwire identification information, anatomical structure identification information (e.g., AC, PC, MCP and MSP locations) and stimulation programming settings may be stored on a memory device from an external source, which may be read by an image registration module and/or a stimulation programming module. The registration module may display the images in a user interface via which different images may be registered to each other. The stimulation programming module may display the images and estimated VOAs overlaid thereon. An example system according to the present invention is shown in FIG. 22, which includes a surgical planning system 2210, a programming and registration system 2220 and an implantable pulse generator (IPG) 2230. Each component 2210/2220/2230 may be in bi-directional communication with any other of the components. The surgical planning system 2210 may include a surgical planning module 2212. The programming and registration system 2220 may include a stimulation programming module 2222 and an image registration module 2224. Each of the modules 2212/2222/2224 may be stored in a respective device memory together with other modules or data.

In the example system of FIG. 22, the surgical planning system 2210 may constitute the external source. For example, the patient images may be saved onto a CD-ROM. A backup copy of the patient images may be stored in a database within the surgical planning system 2210. After the patient is discharged, the patient may be provided with the CD-ROM for subsequent use at a separate medical facility, e.g., a facility corresponding to the programming and registration system 2220. Alternatively, a clinician may directly transmit the patient images to the programming and registration system 2220 via the Internet, e-mail, a private computer network, etc.

In an alternative embodiment, each of the modules may be co-located in a single device. For purposes of illustration, the surgical planning system 2210 has been shown in FIG. 22 as external to the programming and registration system 2220. However, the external device may be any external source of patient images and may, for example, include other programming devices and/or other surgical planning devices that are not part of the same system.

The memory device may be an SD card, CD, etc. The images may be transferred via a network as well, e.g., using WiFi, bluetooth, hardwired, etc.

Integration Between Surgical Planning and Programming Systems

In embodiments in which the surgical planning system and the programming system are separate systems, e.g., as shown in FIG. 22, information input during surgical planning, including information input inter-operatively, may later be exported to the programming system. For example, a file may be created during the surgical planning stage including information regarding the coordinates of the anatomical structures of the patient's brain and the coordinates of the leadwire. For example, a brain atlas may be registered to a patient's MR. Additionally, the leadwire within the brain may be determined based on a selected arc angle and ring angle of a headframe attached to the patient's head. A method for registering the atlas to the MR may include selecting in the MR the AC, PC, and MSP, by which information the system can determine the way in which the atlas relates to the MR.

Alternatively, the CT and MR may be fused. The atlas may be registered to the MR by selecting in the MR the AC, PC, and mid-sagittal line (or other anatomical landmarks). Then the leadwire can be located relative to the atlas by selecting within the CT a termination point of the leadwire and a point on the shaft of the lead. Certain leadwires include a substantially rigid portion (e.g., a portion including the electrode contacts) extending upward from the implanted tip of the leadwire, and a more flexible portion distal from the implanted tip. Since the flexible portion may be bent, selection of a point along the flexible portion may result in an inaccurate trajectory determination. It may therefore be preferable to select a shaft point on the rigid portion of the leadwire.

Either way, the above information may be stored using a surgical planning and performance module in a file that may be transmitted/provided to a separate programming system/module, e.g., by e-mail or physically removing a storage device from a first system and inserting it into the other system. Indeed, the features described above with respect to image registration/scaling, atlas registration/scaling, overlay controls, stem and pivot controls, scaling, feature extraction, etc. may be provided in an image registration/programming system or may be provided in a surgical planning system, e.g., prior to a surgery in which a leadwire is implanted. Data obtained by use of such features in a surgical planning system may then be transferred to another system. Other information that may be transferred from a surgical planning system includes, for example, target and/or side effect VOAs, MER data (e.g., used for updating an atlas, which atlas information may also be transferred).

The programming system/module is configured for reading the file generated by the surgical module, and displaying graphical information overlaid on the registered MR and CT scans, with the registered model as obtained from the surgical module.

Export Patient Data to an External Source

Patient data, such as brain images (pre-implantation and/or post-implantation), clinical notes, leadwire identification information, anatomical structure identification information (e.g., AC, PC, MCP and MSP locations) and stimulation programming settings, may be exported from the registration/programmer module of one computer to that of another computer so that different clinicians can use the information for programming a patient.

In an example embodiment, the system is configured such that the information can be transferred to and obtained from the IPG so that the information travels with the patient. Whenever a computer having a registration and/or programmer module links up with the IPG, it can view the information stored thereon for use to program the IPG for a stimulation therapy.

Example information that can be transferred include program settings, registration information, including position of AC, position of PC, position of the MSP, leadwire tip, another point along the leadwire shaft, explored VOA regions, notes regarding the VOAs, etc.

The memory device used for the export may be an SD card, CD, etc. The network used for the export may be, e.g., using wifi, bluetooth, hardwired, etc.

The computer may allow the information to be modified and may store the new information to the IPG, either as a new data file or by overwriting the older information. In this manner, a clinician or other user of the computer may specify a new set of stimulation parameters for the patient. The new stimulation parameters may be generated in response to a determination that the old stimulation parameters are no longer effective or need to be improved, e.g., due to changes in the orientation of the leadwire or the patient's anatomy or due to changes in patient condition. Other changes to the information include updates to the explored VOA regions, along with notes regarding the explored regions.

Select Target or Side Effect Volume Based on Image Registration to MR from a Patient Population In an example embodiment, the system may store in a database MRs of a patient population, for whom efficacious volumes have been previously determined. For example, stimulation parameters may be applied for members of the patient population, for which application of stimulation parameters, the system may compute a respective estimated VOA. Further, information regarding the efficacy of the parameters, either sensed or received as user-input, may be obtained. The system may thus store information indicative of which VOAs are efficacious for a plurality of members of a patient population, further associated with respective MRs.

The system may select one of the members of the patient population on which to base a determination of a target VOA for the subject patient. Such selection may be made based on any similarity that is of clinical significance, including similarities between the MRs as a whole, similarities between certain predefined portions of the MRs, similarities of MER data, of clinical profiles, ages, sex, etc. With respect to similarities between certain portions of the MRs, the portions on which to perform the image matching may depend on the clinical profile of the patient, as described above in regards to automated atlas registration using rigid, affine, B-Spline registration.

The system may register the MR image of the selected member of the patient population to the MR image of the subject patient. Alternatively, the system may select a subset of the members of the patient population and register a composite image (e.g., an average image) formed by the MR images of the members of the subset to the MR image of the subject patient. The selection of the subset may be based on factors described in detail above in other discussions of a selection of a subset of a patient population.

Registration of the MR images may be manual. For example, a clinician may interact with a user interface to overlay the two MR images correctly aligned translationally and rotationally, and then scale, e.g., the selected MR image to the patient MR image, e.g., according to the methods described in the '330, '312, '340, '343, and '314 applications concerning FIGS. 9 and 10 of the '330, '312, '340, '343, and '314 applications, and/or by any other method described above for registering an atlas to an MR image.

Alternatively, registration of the MR images may be performed automatically using any of the methods described above for registering an atlas to an MR image.

Once the MR images are registered, e.g., the user inputs information indicating that the manual registration is completed, or navigates away from a registration interface to a programming interface, or the automatic registration is completed, the system may use the efficacious VOAs of the member(s) of the patient population whose MR image has been registered as a target VOA in the registered space. For example, the recorded VOA may be warped along with its associated MR image to the subject MR image, resulting in a target VOA within the space of the patient MR image. Alternatively, a spatial relationship of the recorded VOA to the registered patient population MR image may be translated to the warped version of the patient population MR image, thereby defining the spatial relationship of the target VOA relative to the subject patient MR image.

In an alternative example embodiment, the MR images are not registered to each other. Instead, once a member of the patient population is selected based on similarities to the subject patient, the system may translate the relationship of a VOA recorded for the member of the patient population to predetermined structures within the MR image of the selected member to the structures within the MR image of the subject patient to form a target VOA for the subject patient. For example, the system may perform a surface extraction, as described above, in each of the MR images, and based on the position of the VOA relative to the extracted surfaces in the member MR image, the system may determine a VOA for the subject patient having the same relative position with respect to the extracted surfaces in the patient MR image. Alternatively, the system may register an atlas to the member MR image and to the patient MR image, and select as the target VOA, a VOA that has a relative position to surrounding structures of the patient atlas that is the same as the relative position of the VOA of the member of the patient population to the atlas structures of the atlas of the member of the patient population.

The determination of the target VOA for the subject patient need not be a one-time occurrence. Instead, new target VOAs may be generated for the subject patient when, for example, a VOA not previously considered is found to be particularly effective for at least one patient of the subset of patients to which the subject patient has been registered, or for at least one patient of a subset of patients who were associated based on similarities with the subject patient.

While the discussion above concerns determining a target VOA based on previously determined efficacious volumes of a patient population, the system may alternatively or additionally determine side effect volumes, e.g., which are to be avoided as much as possible during stimulation of the patient, based on recorded side effect volumes of the patient population, by performing the steps described with respect to the determination of a target VOA.

Auto-Determine which Lead and IPG to Use Based on the Target Lead Location, Trajectory, and VOA Based on input regarding the target location at which the tip of the leadwire is to be located and the desired trajectory of the leadwire to the target location, and further in view of a target volume of activation (VOA), the system may, e.g., during a surgical planning stage, determine and output a suggested leadwire to use and a suggested implantable pulse generator (IPG) to use as the source for the stimulation pulses (aside from outputting which stimulation parameters to use). Further, in an example embodiment, a user may input the desired trajectory without indicating the target at which the leadwire is to terminate in the patient, e.g., the patient's brain, and the system may further output a suggested depth of implantation of the leadwire to be able to achieve an estimated VOA closest to a target VOA. The system may make these determinations based on a stored atlas of anatomical structures, e.g., a brain atlas, registered to the patient's anatomy, relative to which the input trajectory is defined. For example, a headframe may be positioned or located relative to the patient's head, and the trajectory may be defined by an arc and ring angle relative to the headframe. The atlas may be registered, for example, to an MR image of the patient, as described in detail with respect to the atlas registration sections.

Certain leadwires have rotational electrodes that extend around the entire perimeter of the leadwire (i.e., non-directional electrodes), while others include a plurality of electrodes at a single cross-section of the leadwire, each extending about a respective portion of the perimeter of the leadwire that is less than the entire perimeter.

As for IPGs, certain IPGS are configured to turn on electrodes all at the same amplitude, while other IPGs are configured to output different amplitudes for different electrodes.

If the target VOA is positioned at one side of the leadwire, then application of current at equal amounts all around the leadwire would produce a VOA of which a large portion is to a side of the target VOA. For example, in FIG. 23, a leadwire 2300 having electrodes 2301 to 2306 is positioned to one side of a target VOA 2310. The system may therefore recommend a leadwire that has the multiple electrodes at a single cross-section, and an IPG that is configured for applying different amplitudes at different electrodes so that a current field may be produced for producing a VOA predominantly extending from the leadwire biased in certain directions, rather than equally about the leadwire, in order to better match a target VOA that is biased towards certain sides of the leadwire. For example, signals may be applied to electrodes 2302/2303/2306 may be of higher amplitude than signals applied to electrodes 2301/2304/2305. Further, among the electrodes 2302/2303/2306, the electrode 2303 may have the highest amplitude signal because it is nearest the center of the target VOA 2310.

The target VOA may be expressly input or may be determined automatically, e.g., based on input regarding the patient conditions and information regarding effective VOAs in a patient population.

The system may also provide a recommendation of which leadwire to use when there exist a plurality of potential leadwires. Referring to FIG. 24, a set of leadwires 2401/2402 may be located within or near a target VOA 2400. The system may also estimate VOAs based on various stimulation parameters to determine which of the leadwires 2401/2402, in combination with a particular IPG, provides an estimated VOA that best-matches the target VOA 2400. For example, the leadwire 2401 may provide a better match because it has electrodes nearer a center of the VOA, and is therefore able to provide an estimated VOA covering more of the target VOA 2400 for the same amount of signal (e.g., pulse, frequency, or amplitude) compared to an estimated VOA provided by the leadwire 2402.

The type of IPG used may also be taken into consideration. If an IPG is available that is capable of outputting signals at different levels for different electrodes, the system may estimate VOAs for each leadwire based on the application of the different signals to corresponding directional electrodes in the leadwires. However, if the IPG can only output a single level signal, the system may only estimate VOAs based on the same signal being applied to each of the electrodes in a given leadwire.

The results of estimating VOAs on the leadwires 2401/2402 may therefore indicate that, although both leadwires 2401/2402 are capable of providing a matching estimated VOA given the right input(s), the leadwire 2401 is the superior choice because it would only require a single-level output IPG with a lower power output, whereas the leadwire 2402 would require a multi-level output IPG with a higher power output.

Display Representation of Volume Capable of Stimulation (VCS)

It may be unsafe to apply greater than a certain threshold amplitude. The system may graphically identify areas which are estimated to be stimulatable only with amplitudes that exceed a safe amplitude and/or that are estimated as not being stimulatable with even the highest amplitude settings. For example, the system may grey out such a region, leaving in non-greyed out color the remaining region which is estimated to be stimulatable with a safe amplitude setting. Display of such a region may be useful for a clinician to determine regions on which to focus for finding suitable VOAs and corresponding stimulation parameters.

Referring to FIG. 25, the system may display an estimated VOA 2501 based on the application of specific stimulation parameters to a leadwire 2500. A region 2502 extends inward from infinity towards the estimated VOA 2501 and is bounded by a region 2503, which defines the maximum safely stimulatable region.

In an example embodiment, the system may also determine whether the estimated VOA 2501 is fully-contained within the region 2503. This determination may be repeated as the clinician varies the stimulation parameters to simulate new VOAs. If an estimated VOA breaches the region 2503, the system may highlight the overlapping portions, e.g., in red.

Pre-Compute VOA in a Background Thread

To avoid a delay between receipt of input of stimulation parameters and output of the estimated VOA corresponding to the input stimulation parameters, the system may pre-compute respective VOAs for certain stimulation parameter sets even before receipt of user input specifying those parameter sets. The pre-computed VOAs are stored in association with such parameter sets, and, in response to receipt of user input specifying such parameter sets, the system retrieves from memory and displays the pre-computed VOAs.

It is impractical to pre-compute VOAs for all possible parameter sets. Instead, the pre-computation is for a set of likely parameter sets to be user-input, the likelihood being determined from the active parameter sets or the last user-entered parameter sets.

Referring to, for example, FIG. 3g of the '330, '312, '340, '343, and '314 applications, the pre-computation may be for those parameters that are one step removed in + and − directions for each of certain or all directional controls and/or controls for turning on and off the electrodes. Each step may correspond to a predetermined amount of change in input, e.g., a 0.1 change in amplitude.

For example, for each active electrode of the last entered parameter set, there may be a respective arrow control to increase or decrease the amplitude of the applied current. Therefore, the processor may precompute VOAs for each parameter set where the amplitude for any one of the electrodes is increased and where the amplitude for any one of the electrodes is decreased. For example, the top-right electrode is shown to be at amplitude of 2.7. The system may therefore pre-compute a VOA for where the amplitude of that electrode is 2.6 and for where the amplitude of that electrode is 2.8.

Additionally, arrow controls may be provided for shifting the current field as a whole, as formed by the combination of the various activated electrodes of the last entered stimulation settings, upwards, downwards, to the right, or to the left. Therefore, the system may pre-compute the VOAs for the settings corresponding to one such shift downwards from the current settings, one such shift upwards from the current settings, one such shift to the right from the current settings, etc.

Additionally, certain electrodes may be on and others off. In an example embodiment, the system therefore also pre-computes the VOA for the amplitude setting that would be first set in response to the user selecting the electrode to be turned on. In an example embodiment, when the subject electrode is to be turned on, the system is configured to select an amplitude setting for the subject electrode in view of the amplitude setting(s) of other electrodes in the same leadwire.

Compared to the present settings, the system may pre-compute the VOA for settings corresponding to the turning on of any one of the electrodes that are off according to the present settings. For leadwires with non-directional electrodes, it may be assumed that the subject electrode would be turned onto the same amplitude setting of an adjacent turned-on electrode or, if no adjacent electrode is currently turned on, of the closest turned-on electrode.

Additionally, for non-directional electrodes, the system may pre-compute the VOA assuming that the electrode would be turned onto the same amplitude as that of a most recently modified neighboring electrode (modification can include the turning on of the electrode in addition to changing its amplitude). For example, referring to FIG. 23, if the electrode 2302 is to be turned on, and both the electrodes 2301/2303 have already been turned on, the system may apply to the electrode 2302 the same amplitude as that of whichever one of the electrodes 2301/2303 was most recently modified.

For leadwires with directional electrodes located on the same level (e.g., electrodes at the same longitudinal distance along the leadwire), the system may set the amplitude of the subject electrode to be the same as that of an activated electrode on the same level. Where there are a plurality of activated electrodes on the same level, or where there are no activated electrodes on the same level, the system may apply the procedure described above, in which the amplitude of the most recently modified electrode is used. Referring to FIG. 23, if the electrode 2305 is activated, the system may set the amplitude of the electrode 2302 to be the same as the electrode 2305, even if one of the electrodes 2301/2303 was turned on more recently than the electrode 2305. Thus, the system may accord priority to electrodes on the same level.

In an example embodiment of the present invention, when the leadwire includes directional electrodes, the system may also be configured to pre-compute the VOA assuming a clockwise or counterclockwise rotational shifting of the entire field. Rotational shifting is described, for example, in the '330, '312, '340, '343, and '314 applications in connection with FIGS. 19 to 22. The system may pre-compute the VOA based on a single clockwise and/or counterclockwise step (e.g., rotationally shifting the inputs by one electrode).

The number of VOAs pre-computed in response to a change in user input, as well as the total number of stored pre-computed VOAs, may vary depending on hardware and timing constraints. For example, the number of pre-computed VOAs may be a function of processor speed and/or memory size. In one example embodiment, the system may maintain a cache for storing the pre-computed VOAs, update the cache to include newly pre-computed VOAs, and to delete older pre-computed VOAs, e.g., on a first-in-first-out basis.

Programming and Registration System

In an example embodiment, a system according to the present invention may include a patient registration system 2610 as shown in FIG. 26. The registration system 2610 may be communicatively connected to an IPG 2680, which is in turn communicatively connected to a stimulation electrode 2690. The registration system 2610 may implement any of the modules described above, and may include a processor 2612, a memory device 2614, a communication device 2618 and a user interface 2620.

The processor 2612 may be configured to execute instructions in accordance with the various methods described above. The communication device 2618 may be a media card reader, a telemetry device or any other device by which the registration system 2610 communicates with external devices such as the IPG 2680. The user interface 2620 may include an input device such as a keyboard or mouse, and an output device such as a display monitor.

The memory 2614 may include patient population data 2630, as well as current patient data 2640. As described above, the patient population data may be used for atlas selection. Although shown separately, the current patient data 2640 may be stored as a subset of the patient population data 2630. The patient population data 2630 may include separate databases for various types of patient data, including a scan image database 2631, an atlas database 2632 and a clinical profile database 2633. While the patient population data 2630 is shown in FIG. 26 as being a part of the system 2610, it may instead be stored externally, at a central location accessible via a network by a number of systems. Similarly, the current patient data may be exported to such a central location for updating the patient population data 2630.

The current patient data 2640 may also include similar databases, including a scan image database 2641, a landmark database 2642 and a clinical profile database 2643. The scan image database 2641 includes files corresponding to CT, MR or other imaging modalities, taken before and/or after lead-wire implantation. The landmark database 2642 may include information designating the locations of various brain landmarks, such as the AC, PC, MCP and MSP, relative to an image contained in the scan image database 2641. The clinical profile database 2643 may include, for example, information about the current patient's medical history, the IPG 2680 (e.g., a model number or a serial number assigned to the IPG 2680) and/or the configuration of the stimulation electrode 2690 (e.g., the number and type of the electrode contacts).

The memory 2614 may include any of the various modules described above, as well as additional modules for implementing any of the methods or system features described above. As shown in FIG. 26, this may include for example a pivot/stem tool module 2620, a zoom tool module 2621, an MSP selection module 2622, an AC/PC selection module 2623, a cross-section ID module 2624, a slice scrolling module 2625, an atlas registration module 2626 and an auto image correction module 2627.

System Integration

In an example embodiment of the present invention, systems may be provided in a stand-alone version, where the settings in the stimulation programming module cannot be transferred from the module to the IPG, but instead, the user would have to manually enter the settings the user likes into another module that controls the IPG.

In an example embodiment of the present invention, systems may be provided in a semi-integrated version, where a telemetry device, e.g., the communication device 2618 of FIG. 26, is used for transporting stimulation parameters to the IPG for implementation thereof from a stimulation programming module that computes and outputs an estimated VOA for parameter settings, where the corresponding VOAs for the various parameter settings are displayed for user review. When the user likes a parameter set, the user can input an instruction for the transmission of the settings to the IPG for implementation thereof.

In an example embodiment of the present invention, systems may be provided in a more fully integrated version, where a telemetry device is used for transporting stimulation parameters to the IPG for implementation thereof from a stimulation programming module that computes and outputs an estimated VOA for parameter settings, where the parameters are sent automatically. For example, if the current patient or a patient in the patient population self-reports a particular side-effect or a benefit, or exhibits a measured side-effect/benefit in response to clinician-supervised testing, and/or in response to sensor output, the system may automatically determine a new set of stimulation parameter settings by adjusting the existing stimulation parameters, e.g., in step-wise fashion according to the VOA pre-computation described above. The system may adjust the stimulation parameter settings so as to decrease activation in areas of the brain associated with the reported side effect or to increase activation in areas of the brain associated with the reported benefit. As a safety measure, the system may only be allowed to automatically adjust the existing stimulation parameter settings within a predetermined range of parameter values, e.g., a maximum allowable change in amplitude. The system may also be time-constrained by limiting automatic adjusting to a maximum allowable number of adjustments in a given time period, e.g., once per day, or to a mandatory waiting period between adjustments, e.g., twelve hours.

The above description is intended to be illustrative, and not restrictive. Those skilled in the art can appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

What is claimed is:

1. A system for associating anatomical information with image data, the system comprising:
   a computer processor configured to:
   obtain, via user input, an identification of a location of an anatomical landmark within a three-dimensional space formed by the image data, wherein the image data includes a first image that is of a first two-dimensional slice of the three-dimensional space and a second image that is of a second two-dimensional slice of the three-dimensional space, the second two-dimensional slice being orthogonal to the first two-dimensional slice;
   record the identified location in association with the image data; and
   display a first graphical representation of the anatomical landmark overlying a display area in which the first image is displayed and a second graphical representation of the anatomical landmark overlying a display area in which the second image is displayed;
   wherein the user input includes one of:
   an instruction for rotating the first image relative to the first graphical representation of the anatomical landmark and an instruction for rotating the second image relative to the second graphical representation of the anatomical landmark; and an instruction for rotating the first graphical representation of the anatomical landmark relative to the first image and an instruction for rotating the second graphical representation of the anatomical landmark relative to the second image.

2. The system of claim 1, wherein the anatomical landmark is a predefined plane.

3. The system of claim 2, wherein the image data is of a brain and the plane is a mid-sagittal plane (MSP).

4. A system for associating anatomical information with image data, the system comprising:
a computer processor configured to:
obtain user input of a location of an anatomical landmark within a three-dimensional space formed by the image data, wherein the anatomical landmark is a predefined plane, and the user input includes selection of three points within the three-dimensional space, at least two of the three points being selected in different displayed imagoes; and
in response to the selection of the three points, update a display area in which an image in which none of the three points is selected is displayed to display a different image that corresponds to the plane.

5. The system of claim 4, wherein the image data is of a brain and the plane is a mid-sagittal plane (MSP).

6. A system for associating anatomical information with image data, the system comprising:
a computer processor configured to:
obtain locations of at least two anatomical landmarks within a three-dimensional space formed by the image data:
register an anatomical structure atlas to an anatomical region represented in the image data based on the obtained locations of the at least two anatomical landmarks:
wherein:
the registration includes:
aligning the anatomical structure atlas with the image data; and
in accordance with the obtained location, scaling the anatomical structure atlas:
the scaling includes modifying the anatomical atlas structure such that at least two anatomical landmarks of the anatomical atlas structure, that correspond to the at least two anatomical landmarks whose locations were obtained, are offset from a predefined anatomical structure of the anatomical structure atlas relative to other structures of the anatomical structure atlas equal to an offset of the obtained locations of the at least two anatomical landmarks to a location defined in the image data as corresponding to the predefined structure, relative to remaining portions of the anatomical region represented in the image data.

7. The system of claim 6, wherein the processor is configured to record the scaled anatomical structure atlas in association with a subject to whom the anatomical region belongs.

8. The system of claim 6, wherein the predefined anatomical structure is a mid-commissural point (MCP).

9. A system for associating anatomical information with image data, the system comprising:
a computer processor configured to:
obtain an identification of locations of an anterior commissure (AC) point and a posterior commissure (PC) point within a three-dimensional space formed by the image data:
select a point between the AC point and the PC point as a mid-commissural point (MCP) defined in an anatomical region represented in the image data; and
register an anatomical structure atlas to the anatomical region represented in the image data, wherein the registration includes:
aligning the anatomical structure atlas with the image data based on the selection; and
based on a distance between the MCP defined in the anatomical region and the identified AC point and PC point, scaling the anatomical structure atlas.

10. The system of claim 9, wherein the anatomical structure atlas is non-linearly scaled, such that, the further a region of the anatomical structure atlas is from the MCP, the less the region is modified by the scaling.

11. The system of claim 9, wherein the anatomical structure atlas is anisotropically scaled.

12. A system for associating anatomical information with image data of a patient, the system comprising:
a computer processor configured to:
obtain a location of an anatomical landmark within a three-dimensional space formed by the image data; and
generate a patient-specific anatomical atlas, wherein the generation includes at least one of:
(A) registering an anatomical atlas to the patient image data with a combination of a rigid registration, an affine registration, and a B-spline registration; and
(B) performing the following:
registering each of a plurality of anatomical atlases to the patient image data;
determining similarities between image data corresponding to the plurality of anatomical atlases and the patient image data; and
in accordance with the determined similarities, combining at least two of the registered anatomical atlases.

13. The system of claim 12, wherein the generation includes (B), and the plurality of anatomical atlases are image data sets corresponding to a patient population, atlas structures having been previously defined in the image data sets.

14. The system of claim 12, wherein the generation includes (B), and different weights are applied to different ones of the at least two anatomical atlases corresponding to different degrees of similarity between the different ones of the at least two anatomical atlases and the patient image data.

15. The system of claim 12, wherein the generation includes (B), and the registration further includes applying the rigid registration.

16. The system of claim 15, wherein the registration further includes applying the affine registration.

17. The system of claim 16, wherein the registration further includes applying the B-spline registration.

18. The system of claim 17, wherein the affine registration is applied subsequent to the application of the rigid registration.

19. The system of claim 17, wherein the registration further includes performing a skull stripping on the image data prior to the application of the rigid registration.

20. The system of claim 15, wherein the registration further includes performing a skull stripping on the image data prior to the application of the rigid registration.

21. The system of claim 12, wherein the generation includes (A), and one of:
the rigid registration is followed by the affine registration, and the affine registration is followed by the B-spline registration; and
the processor is further configured to strip skull data from the image data prior to the rigid registration.

22. The system of claim 12, wherein the generation includes (A).

23. The system of claim 12, wherein the generation includes (B).

24. A system for associating anatomical information with image data that represents an anatomical region, the system comprising:
a computer processor configured to:
obtain a location of at least two anatomical landmarks within a three-dimensional space formed by the image data;
align an anatomical structure atlas with the image data; and
in accordance with the obtained location, scale the anatomical structure atlas;
wherein one of:
the scaling of the anatomical structure atlas is non-linear, such that the further a region of the anatomical structure atlas is from a defined mid-commissural point (MCP), the less the region is modified by the scaling;
the anatomical structure atlas is anisotropically scaled, the anatomical structure atlas is of a brain, and the scaling includes modifying the anatomical structure atlas in each of left and right directions and a superior and inferior directions by approximately 0.8 an amount by which the anatomical structure atlas is modified in anterior and posterior directions; and
the anatomical structure atlas is anisotropically scaled, the anatomical structure atlas is of the brain, and the scaling includes modifying the anatomical structure atlas in each of the left and right directions and the superior and inferior directions by 0.8 the amount by which the anatomical structure atlas is modified in the anterior and posterior directions, plus 0.2.

25. The system of claim 24, wherein the non-linear scaling is performed.

26. The system of claim 24, wherein the anatomical structure atlas is of the brain, and the scaling includes the modification of the anatomical structure atlas in each of the left and right directions and the superior and inferior directions by approximately 0.8 the amount by which the anatomical structure atlas is modified in the anterior and posterior directions.

27. The system of claim 24, wherein the anatomical structure atlas is of the brain, and the scaling includes the modification of the anatomical structure atlas in each of the left and right directions and the superior and inferior directions by 0.8 the amount by which the anatomical structure atlas is modified in the anterior and posterior directions, plus 0.2.

* * * * *